United States Patent
Trapero Martin

(10) Patent No.: US 11,156,965 B1
(45) Date of Patent: Oct. 26, 2021

(54) LATCHING MECHANISM FOR SECURING TWO OBJECTS

(71) Applicant: ANEXA LABS LLC, Mountain View, CA (US)

(72) Inventor: Ana Trapero Martin, Salamanca (ES)

(73) Assignee: ANEXA LABS LLC, Mountain View, CA (US)

( * ) Notice: Subject to any disclaimer, the term of this patent is extended or adjusted under 35 U.S.C. 154(b) by 0 days.

(21) Appl. No.: 17/078,926

(22) Filed: Oct. 23, 2020

Related U.S. Application Data

(63) Continuation of application No. 17/078,657, filed on Oct. 23, 2020.

(51) Int. Cl.
| | |
|---|---|
| G04B 37/14 | (2006.01) |
| A44C 5/14 | (2006.01) |
| A44C 5/20 | (2006.01) |
| G04G 17/04 | (2006.01) |
| G06F 1/16 | (2006.01) |
| A44B 11/25 | (2006.01) |

(52) U.S. Cl.
CPC ...... G04B 37/1486 (2013.01); A44B 11/2596 (2013.01); A44C 5/147 (2013.01); A44C 5/2085 (2013.01); G04B 37/148 (2013.01); G04G 17/04 (2013.01); G06F 1/163 (2013.01)

(58) Field of Classification Search
CPC .. G04B 37/148; G04B 37/1486; G04G 17/04; G06F 1/163; A44B 11/2596; A44C 5/147; A44C 5/2085
See application file for complete search history.

(56) References Cited

U.S. PATENT DOCUMENTS

| | | | |
|---|---|---|---|
| 9,237,869 B1 | 1/2016 | Lee | |
| 9,445,633 B2 * | 9/2016 | Tulloch | H01R 31/06 |
| 9,913,591 B2 | 3/2018 | Lapetina et al. | |
| 10,058,149 B1 * | 8/2018 | Wittenberg | H01R 13/639 |
| 10,285,475 B1 * | 5/2019 | Tully, Jr. | A44C 15/005 |
| 10,327,520 B1 * | 6/2019 | Ely | G04B 37/12 |
| 2003/0050010 A1 | 3/2003 | Fallenstein | |
| 2005/0217080 A1 * | 10/2005 | Kojoori | A44C 5/14 24/265 WS |
| 2008/0146871 A1 | 6/2008 | Ameson | |
| 2009/0058635 A1 | 3/2009 | LaLonde | |
| 2009/0177033 A1 | 7/2009 | Hendriks | |

(Continued)

FOREIGN PATENT DOCUMENTS

| | | | | |
|---|---|---|---|---|
| GB | 2147717 A | * | 5/1985 | A44C 5/22 |

OTHER PUBLICATIONS

U.S. Appl. No. 17/078,657, filed Oct. 23, 2020, Martin, Ana Trapero, Wearable Device for Monitoring Health Metrics.

(Continued)

*Primary Examiner* — Daniel P Wicklund
(74) *Attorney, Agent, or Firm* — Nixon Peabody LLP

(57) ABSTRACT

A latching mechanism for connecting a first object to a second object is provided. The latching mechanism includes a groove provided along a surface of the first object. The groove includes a notch. The notch can be centered in the groove. The groove is configured to receive a connective end of the second object, and the notch is configured to lock the connective end of the second object in place. The notch can receive a tab from the connective end of the second object.

6 Claims, 30 Drawing Sheets

(56) References Cited

U.S. PATENT DOCUMENTS

| | | |
|---|---|---|
| 2011/0022411 A1 | 1/2011 | Hjelm |
| 2012/0149981 A1 | 6/2012 | Khait |
| 2012/0197144 A1 | 8/2012 | Christ |
| 2012/0271121 A1 | 10/2012 | Della Torre et al. |
| 2013/0116534 A1 | 5/2013 | Woo |
| 2013/0338448 A1 | 12/2013 | Libbus |
| 2014/0135609 A1 | 5/2014 | Kostenich |
| 2014/0275850 A1 | 9/2014 | Venkatraman |
| 2015/0212541 A1* | 7/2015 | Lu .................. A44C 5/14 361/679.03 |
| 2015/0351690 A1 | 12/2015 | Toth |
| 2016/0022210 A1 | 1/2016 | Nuovo et al. |
| 2016/0029911 A1 | 2/2016 | Lee |
| 2016/0037876 A1* | 2/2016 | Perkins .............. A44C 5/2085 224/164 |
| 2016/0040698 A1* | 2/2016 | Perkins .............. A44C 5/2085 24/664 |
| 2016/0192856 A1 | 7/2016 | Lee |
| 2017/0181510 A1* | 6/2017 | Novak ................ A44C 5/185 |
| 2017/0296092 A1 | 10/2017 | Jones |
| 2018/0026393 A1 | 1/2018 | Eid |
| 2018/0026678 A1 | 1/2018 | Biederman |
| 2018/0042502 A1 | 2/2018 | Wang |
| 2018/0214079 A1 | 8/2018 | Banet |
| 2018/0249767 A1 | 9/2018 | Begriche |
| 2018/0287115 A1 | 10/2018 | Strong |
| 2019/0082968 A1 | 3/2019 | Karnik |
| 2019/0261888 A1 | 8/2019 | Zdeblick et al. |
| 2020/0144777 A1 | 5/2020 | Chahine |
| 2020/0202083 A1 | 6/2020 | Vartiovaara |
| 2020/0397315 A1 | 12/2020 | Raj |

OTHER PUBLICATIONS

U.S. Appl. No. 17/078,926, filed Oct. 23, 2020, Martin, Ana Trapero, Latching Mechanism for Securing Two Objects.

* cited by examiner

LATCHING MECHANISM FOR SECURING TWO OBJECTS

CROSS-REFERENCE TO RELATED APPLICATIONS

This application is a continuation of U.S. patent application Ser. No. 17/078,657, filed Oct. 23, 2020, which is hereby incorporated by reference in its entirety.

TECHNICAL FIELD

The present disclosure relates to monitoring health metrics of a user and more specifically to systems, methods, and devices that integrate a plurality of sensors in a compact form factor to capture measurements for determining the health status of the user. The present disclosure also relates to an electronic device that uses a modular design to integrate various sensor units and functionalities to monitor health-related metrics at different body locations.

BACKGROUND

Wearable devices are becoming ubiquitous in society. These devices are worn on the human body and are designed to measure one or more biological and environmental parameters. Smartwatches and smart patches are examples of wearable devices that can have multiple sensors and that can pair to a smartphone, tablet, computer, or another connected device. Smartwatches can provide estimates of the activity level of a human in the form of the number of steps the human takes per day. Smartwatches can provide a heart rate of the human, a location of the human, and so on. Smart patches and smartwatches can have similar functionality, e.g., they can both measure health metrics, but both may have different sensors and user interfaces. Smart patches may include a complementary electrode array to record continuous and consistent electrocardiogram (ECG) signals and may not come with a display. Furthermore, unlike smartwatches which can be removed anytime by opening a strap or stretching an elastic band, smart patches typically attach to a user via some type of adhesive.

Some smart patches (e.g. a cardiac patch monitor) can acquire and present ECG readings more efficiently, surpassing the ECG monitoring performance of a smartwatch. To capture ECG data, smartwatches sometimes use an electrode integrated on the back of the watch housing which comes in contact with the skin, and another electrode embedded in the smartwatch's crown. Placing a finger from the opposite hand on the smartwatch's crown completes a circuit between the user's heart and arm that allows the smartwatch to record electrical impulses across the chest. Furthermore, a smart patch can have higher quality ECG readings as a result of employing more than one ECG lead for signal acquisition, and also due to positioning the smart patch on the user's chest, such that the smart patch is in close proximity to the user's heart. Thus, a versatile device that can operate as a smartwatch or a smart patch for capturing ECG signals can provide more accurate results compared to a smartwatch that can only be positioned on the wrist of a user. The present disclosure provides benefits of employing a convertible device that can function as either a smartwatch or a smart patch, compared to single-purpose wearable devices. The present disclosure avoids drawbacks associated with collecting health metrics of a user from a single-purpose wearable device and provides other advantages.

SUMMARY

According to some implementations of the present disclosure, an electronic device is provided. The electronic device includes a housing forming an enclosed chamber. The housing has a top portion and a bottom portion. The electronic device further includes one or more sensors provided within the chamber and configured to interface with a user to generate physiological data associated with the user. The electronic device further includes a set of electrodes provided on the bottom portion of the housing. Each electrode in the set of electrodes is a single member having a corresponding inner electrode portion within the chamber and an outer electrode portion outside the housing. In some embodiments, the electronic device further includes a set of magnets provided on the bottom portion of the housing. In some embodiments, the electronic device can couple to a strap.

In some embodiments, the electronic device can couple to a patch housing. The patch housing includes a patch assembly, which includes a flat substrate having a first surface and a second surface with adhesive on at least one of the first or second surfaces. The substrate further includes at least one opening. The patch assembly further includes a set of electrodes provided in the second surface of the substrate. The patch assembly further includes a set of connectors on the first surface of the substrate, with at least some of the connectors being configured to mechanically couple the electronic device to the substrate. In some embodiments, some of the connectors on the first surface of the substrate of the patch assembly are configured to electrically couple with a set of electrodes provided in the second surface of the substrate. In some embodiments, the patch housing includes a case body for shielding the electronic device from environmental elements when the electronic device is coupled to the patch housing.

According to some implementations of the present disclosure, a latching mechanism for connecting a first object to a second object is provided. The latching mechanism includes a groove provided along a surface of the first object. The groove includes a notch. The groove is configured to receive a connective end of the second object, and the notch is configured to lock the connective end of the second object in place. In some embodiments, the first object is an electronic device and the second object is a strap. In some embodiments, the connective end of the strap includes a tab that locks the strap within the groove, preventing the strap from laterally sliding along the groove.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
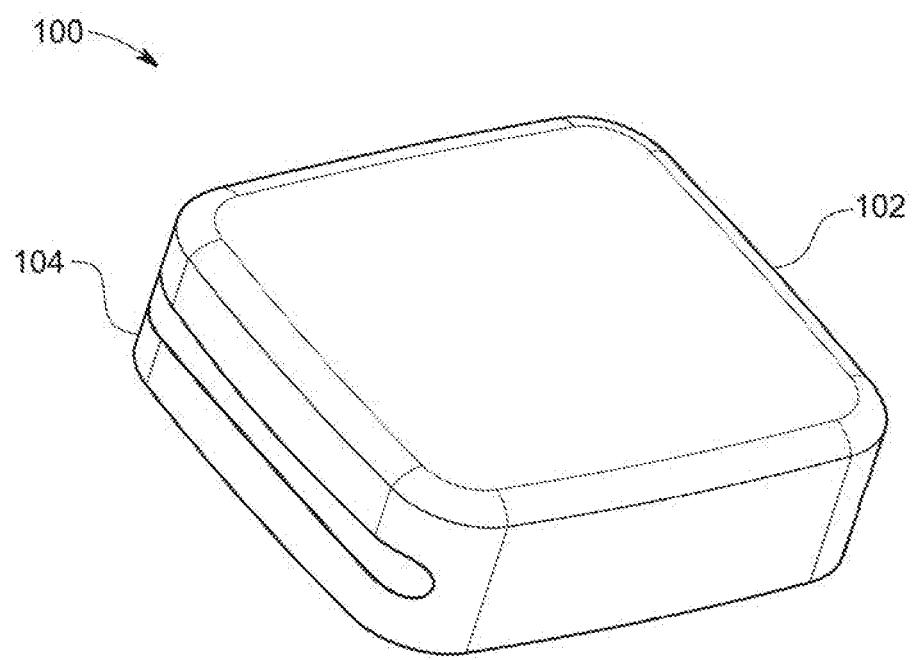
FIG. 1 illustrates an electronic device for monitoring health metrics of a user, according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

In the present disclosure, the term "component" or "module", as used hereinafter, defines, without being limited to, a software or hardware component which performs certain tasks. A component or module may advantageously be arranged to one or more different functionalities enabled by the module's software and hardware components.

Embodiments of the present disclosure provide an electronic device that can be configured as either a smartwatch or a smart patch. In a smart patch configuration, the electronic device has the potential to enable many possible ECG lead arrangements from the same device, which allows for higher quality data from near the heart. An advantage of converting a smartwatch into a Holter monitor type of device, among other wearables, includes the potential of obtaining continuous ECG and other health metric monitoring from a single device. An advantage of electronic devices designed according to some implementations of the present disclosure is that these electronic devices will benefit from scaling down the size of electronic components, thus allowing these electronic devices to integrate more sensors and/or more powerful processors that enable additional functionality or enhance current capabilities.

Some implementations of the present disclosure provide electronic components that can capture health-related metrics of a user using sensors, algorithms, and/or wireless technologies. Wireless technologies can enable remote monitoring capabilities. The electronic devices can be used for recording ECG, heart rate, temperature, blood oxygen saturation (SpO2), blood pressure, blood glucose, body position, activity, and other health metrics. The electronic components can utilize different sensing modules and/or different user interfaces, depending on whether in the smartwatch mode or whether in the smart patch mode.

Some implementations of the present disclosure provide electronic devices that can obtain health metrics or measurements from a user in an unobtrusive manner. The electronic devices can be configured to perform contact and/or non-contact measurements. In some implementations, non-contact measurements are achieved using electromagnetic signaling, optical sensing, etc. In some implementations, contact measurements are achieved using electrodes. In some implementations, the electronic devices have a small form factor and can be modified to perform invasive measurements or deliver drugs or treatments (e.g., insulin) in response to changes in health metrics detected by the device.

The electronic devices can be configured in multiple ways, providing flexibility and other advantages over conventional devices. For example, an electronic device according to some implementations can be decoupled from an adhesive housing so that a battery contained within the electronic device can be charged. The electronic device can be decoupled from the adhesive housing so that watch straps can be attached. When the electronic device is provided in a smart patch configuration and coupled to a substrate with an adhesive, adhesive electrode and/or electronics waste can be reduced when compared to conventional smart patches. In some implementations, the electronic device can be decoupled from the substrate with the adhesive without disturbing the substrate when the substrate is attached to the skin of the user. This prevents detaching and reattaching the adhesive which can damage the skin of the user or damage the adhesive. Furthermore, leaving the substrate with the adhesive in place allows reconnecting the electronic device to the same location, thus reducing or eliminating a need for recalibrating or reconfiguring the electronic device. Using a versatile electronic device allows making measurements at the same location since the substrate with the adhesive was not removed. Therefore, the effect of noise relating to minor location changes is reduced.

Referring to FIG. 1, an electronic device 100 for monitoring health metrics of a user is provided, according to some implementations of the present disclosure. The electronic device 100 can include a housing with a top portion 102 and a bottom portion 104. In some implementations, from a top view, the electronic device 100 has a cross-section shaped like a square with rounded corners; and from a side view, the electronic device 100 has a rectangular cross-section. The top portion 102 and the bottom portion 104 of the housing, when interfacing with one another, form an enclosed chamber. The housing of the electronic device 100 can be made from non-corrosive, chemically resistant material that can withstand high temperature fluctuations. The housing can be made from a rigid material (e.g., aluminum, stainless steel, titanium, plastic composites, polymer composites, ceramics, etc.). In some implementations, the housing can dissipate heat from components within the electronic device 100 or components attached to an exterior of the electronic device 100. In some implementations, the housing can be an electromagnetic shield that blocks or redirects radio frequency radiation away from the user. The electronic device 100 can be of a small form factor such that the user can wear the electronic device 100 comfortably.

Figure 2:
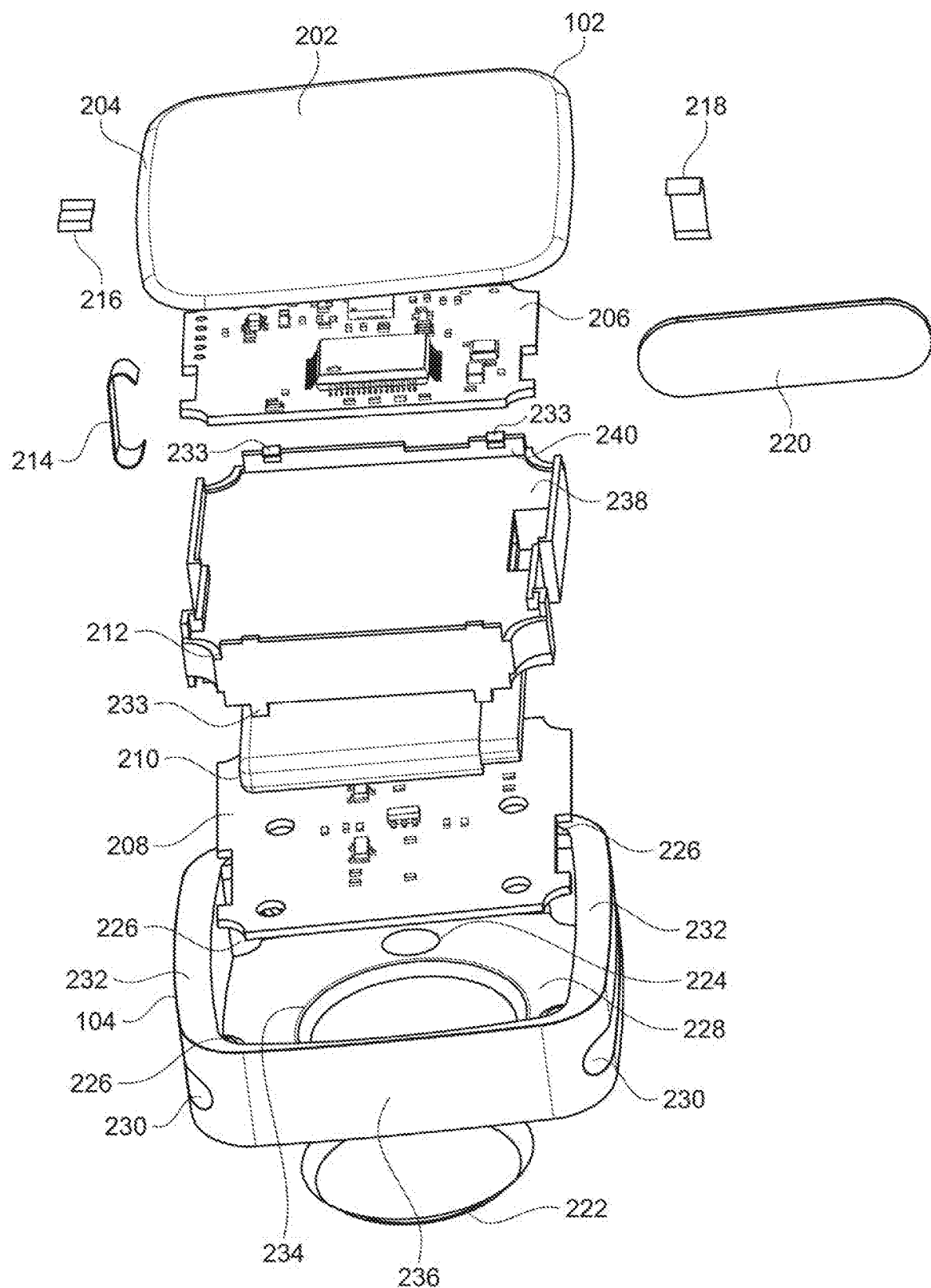
FIG. 2 illustrates components of the electronic device of FIG. 1, according to some implementations of the present disclosure.

Referring to FIG. 2, components of the electronic device 100 of FIG. 1 are illustrated, according to some implementations of the present disclosure. The top portion 102 of the electronic device 100 can include a curved section 204 and a flat section 202. The top portion 102 can be a bezel-less screen that seals components of the electronic device 102 within the enclosed chamber once the bottom portion 104 and the top portion 102 interface with each other. The top portion 102 can include glass that protects the bezel-less screen. In some implementations, the top portion 102 is an integrated glass and screen combination. In some implementations, the screen included in the top portion 102 changes display configuration, conforming the electronic device 100 to show information to the user in different display formats depending on whether the electronic device 100 is operating in one of many modes (e.g., a smartwatch mode, a patch mode, an anklet mode, etc.). The display quality of the screen in the top portion 102 can support a large color and brightness gamut to counteract color washout from ambient light and, to enable text and graphic information to be read by the user. The screen included in the top portion 102 can support a backlit liquid crystal display (LCD) or an organic light-emitting diode (OLED) display. In some implementations, the top portion 102 includes a bezel-less screen technology based on, but not limited to, a thin LCD. The thin LCD can be curved by the edges to achieve a lighter design and avoid any sharp edges, thus reducing any possible damage by a sharp edge to the skin of the user during operation. Thus, the screen can take up at least a portion of the flat section 202 and/or at least a portion of the curved section 204.

In some implementations, the use of the screen included in the top portion 102 can be optimized by automatic brightness calibration and/or a temporized screen saver mode in order to preserve battery life of a battery 210 included in the electronic device 100. A display mode can be set so if the screen is not in use, the screen is turned off. As such, the screen in the top portion 102 does not always have to be on, and may be turned on instantaneously by touching the screen or through interpretation of the user's arm motion and gestures. In some implementations, accelerometers and gyroscopes are used in sensing the user's motion and gestures. In some implementations, a light sensor may be included in the top portion 102 of the housing for brightness correction purposes so that brightness of the screen can be auto-adjusted. In some implementations, an ultraviolet sensor is embedded in the screen of the top portion 102, either alone or in combination with the light sensor. The ultraviolet sensor can be used to measure ultraviolet light exposure throughout a use (e.g., a daily use) of the electronic device 100. In some implementations, reflective, transflective, curved and bendable displays can be incorporated in the screen of the electronic device 100.

The electronic device 100 includes at least one printed circuit board (PCB). In some implementations, the electronic device 100 includes a first PCB 206 and a second PCB 208. The first PCB 206 and the second PCB 208 are arranged in a stack such that the electronic device 100 utilizes space within the enclosed chamber more efficiently. The stacked design also enables the electronic device 100 to have a more compact design compared to conventional devices. Although two PCBs are included in FIG. 2, more than two PCBs can be stacked within the electronic device 100. For example, three PCBs, four PCBs, five PCBs, six PCBs, ten PCBs, etc., can be configured in a stack to conserve space. The two PCBs illustrated in FIG. 2 are merely provided as an example.

The first PCB 206 can include a processor, a microcontroller, a central processing unit, etc., for performing calculations and/or controlling data displayed by the screen included in the top portion 102 of the housing. The first PCB 206 can include memory and/or other storage components that facilitate functions performed by the processor by storing intermediate calculations and/or settings. The memory and/or other storage components can also store health metrics collected by sensors of the electronic device 100. The second PCB 208 can be a sensor PCB for gathering sensor data. The second PCB 208 can include one or more sensors and/or can be connected to one or more electrodes that obtain data from outside of the housing of the electronic device 100. In some implementations, the first PCB 206 is connected to the screen in the top portion 102 using a screen connector 216. The screen connector 216 can be a flexible PCB connector. The screen connector 216 allows the first PCB 206 to control the screen in the top portion 102 for displaying text, images, health metrics, etc.

The first PCB 206 and the second PCB 208 can be separated by the battery 210 and a mechanical holder 212. The holder 212 secures the first PCB 206 in place such that the first PCB 206 lays on a first surface 238 of the holder 212. The holder 212 can include one or more edge protrusions 240 along a perimeter of the first surface 238 that prevents the first PCB 206 from moving laterally once secured in the holder 212. The holder 212 can include multiple tabs 233 that prevent the first PCB 206 and/or the second PCB 206 from moving vertically once secured in the holder 212. The holder 212 can also hold the battery 210 and the second PCB 208 in place below the first PCB 206. In the stack configuration, the first surface 238 separates the battery 210 and the second PCB 208 from the first PCB 206. In the stack configuration, the battery 210 is sandwiched between the first PCB 206 and the second PCB 208. A connector 214 can be provided for connecting the first PCB 206 to the second PCB 208. The connector 214 can be a flexible PCB connector in some implementations. The connector 214 electrically connects the first PCB 206 and the second PCB 208. In some implementations, the connector 214 includes power buses or power rails for sharing power from the battery 210 with a PCB (e.g., the first PCB 206 or the second PCB 208), if at least one of the PCB's (e.g., the first PCB 206 or the second PCB 208) is not directly connected to the battery.

In some implementations, the second PCB 208 is a sensor PCB that gathers data (e.g., physiological data, activity data, stress measures, and/or other types of data) from the user and is coupled to the first PCB 206 via the connector 214, in order to share the gathered data with the first PCB 206. The first PCB 206 can process the data gathered by the second PCB 208. In some implementations, the first PCB 206 can communicate (wired or wirelessly) with other electronic devices (e.g., a laptop, a tablet, a smartphone, or some other computing device). The first PCB 206 can include a near-field communication (NFC) module, a Bluetooth, low energy (BLE) interface, and additional wireless communication interfaces/antenna modules. With respect to NFC capability, there may be an antenna situated proximally to the top of the electronic device 100 (e.g., on the first PCB 206) and/or an antenna situated proximally to the bottom of the electronic device 100 (e.g., on the second PCB 208). In some implementations, both antennas facilitate wireless pairing, wireless charging and contactless transactions.

Examples of contactless transactions include NFC payments, identity type transactions, etc. In some implementations, the antenna situated proximally to the top of the electronic device 100 is used primarily for wireless pairing, communication and contactless transactions, and the antenna situated proximally to the bottom of the electronic device 100 is used primarily for wireless charging when the electronic device 100 is docked on a charging station.

An NFC module included on the first PCB 206 and/or the second PCB 208 can enable proximity-based, rapid setup of wireless pairing between the electronic device 100 to another device (e.g., a smartphone, tablet, or another computing device with supported NFC capabilities). The NFC module can facilitate the automatic launching of one or more applications associated with the electronic device 100 on a smartphone when the smartphone's NFC interface is positioned in proximity to the NFC interface of the electronic device 100. In some implementations, the launched applications on the smartphone can then display real-time health metrics streamed from the electronic device 100.

The electronic device 100 includes the bottom portion 104 of the housing. The bottom portion 104 can include one or more sidewalls 232 and 236. An exterior of the sidewalls 232 can include grooves 230 for attaching a strap to the electronic device 100. An exterior of at least one of the sidewalls 236 can provide spacing for a side touch track 220. In FIG. 2, the side touch track 220 is provided on the exterior of the sidewall (not shown) across from the shown sidewall 236. Although one side touch track 220 on the exterior of the sidewall is described, other arrangements are within the scope of the present disclosure. For example, the side touch track 220 can be provided on the exterior of the sidewall 236, or side touch tracks can be provided on both sidewalls. In some implementations, the electronic device 100 includes a side touch track connector 218 provided inside the electronic device 100. The side touch track connector 218 can be a flexible PCB connector. The side touch track connector 218 connects the side touch track 220 to the first PCB 206 and facilitates the first PCB 206 controlling input/output functionality of the side touch track 220.

The bottom portion 104 can include a plurality of interior corner pieces 226. The interior corner pieces 226 are located between two sidewalls 232 and 236 and project inward within the chamber. Corners of the first PCB 206, the second PCB 208 and the holder 212 are shaped to accommodate the interior corner pieces 226. Conforming the shapes of the first PCB 206, the second PCB 208 and the holder 212 to the interior corner pieces 226 prevents the first PCB 206, the second PCB 208 and the holder 212 from moving when installed in the bottom portion 104 of the housing.

Figure 3:
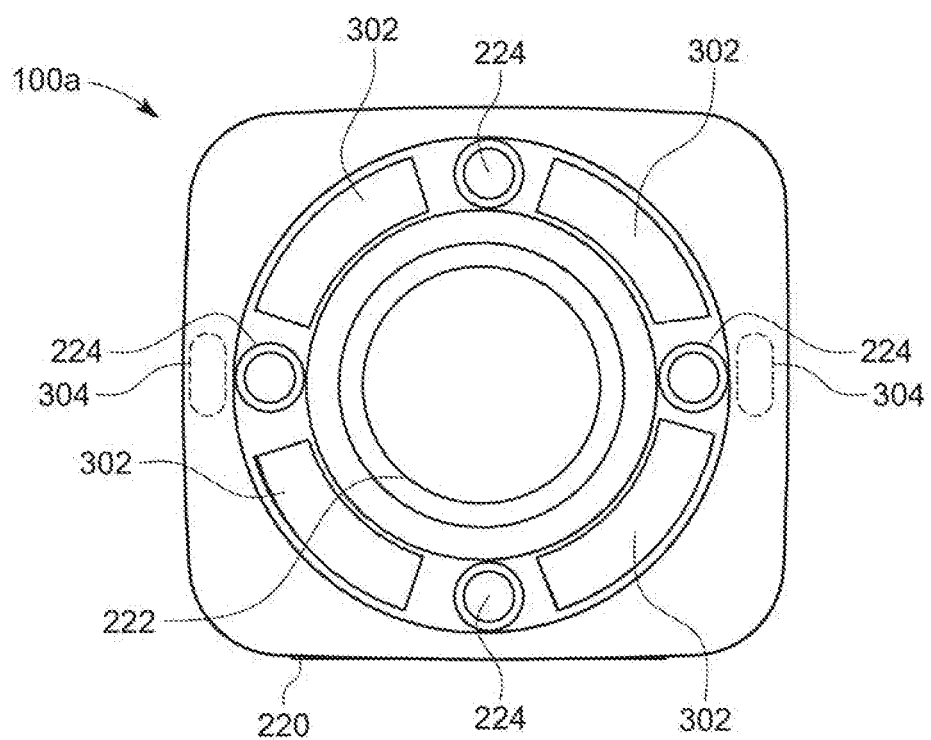
FIG. 3 illustrates a bottom view of a first design of the electronic device of FIG. 1, according to some implementations of the present disclosure.

The bottom portion 104 includes a floor 228 that joins the sidewalls 232 and 236. The floor 228 includes a connecting member 224 and an opening 234 for receiving a housing window 222. The connecting member 224 can be a conducting connector that allows electrical current conduction between the components in the enclosed chamber and the outside environment of the electronic device 100. In some implementations, the connecting member 224 can be a metal electrode that connects the second PCB 208 to an outside environment of the electronic device 100. In some implementations, the connecting member 224 includes a male (or a female) snap connector that can mechanically interface with a female (or a male) counterpart outside the electronic device 100. In some implementations, the connecting member 224 includes a flat electrode, even though FIG. 3 provides the example of the connecting member 224 as a snap connector. In some implementations, a first portion or a first surface of the connecting member 224 borders the enclosed chamber and a second portion or a second surface of the connecting member 224 is outside the housing.

The housing window 222 can have a circular shape, a square shape, a rectangle shape, a polygon shape, an oval shape, etc. The shape of the housing window 222 can be determined by the disposition of sensors on the electronic device 100. The housing window 222 can be translucent or transparent to allow optical sensors, imaging sensors, thermal imaging sensors, laser sensors, radar sensors (e.g., Doppler radar), ultrasonic Doppler flow meters, electromagnetic flow meters, and/or other sensors clear access to the surface of the skin of the user. The housing window 222 can include material for protecting electronic components within the electronic device 100 from outside contaminants (e.g., liquid, dust, and/or other particles). The material of the housing window 222 can include plastic, sapphire crystal, glass, mineral crystal, plexiglass, hesalite crystal, etc. The housing window 222 can integrate lenses to amplify acquisition of sensor data and, in some cases, emission of signals. The housing window 222 can allow sensors within the electronic device 100 (especially sensors on the second PCB 208) to have a closer contact with the skin of the user and also protect electronic components within the electronic device 100.

In some implementations, the battery 210 is a rechargeable lithium polymer (LiPo) battery that can be recharged using the connecting member 224 installed on the floor 228 of the bottom portion 104. In some implementations, the battery 210 can be charged by magnetic and/or other wireless charging technologies. The second PCB 208 can include one or more charging connections for a determined battery arrangement. In some implementations, the electronic device 100 includes at least one NFC module, and a single antenna for the NEC module that are used to enable pairing communications, charging and contactless transactions. The electronic device 100 may adhere to NFC Forum's Wireless Charging Technical Specification (WLC), which uses the 13.56 MHz base frequency and leverages the NFC communication link to control power transfer to the battery 210. NFC technology is beneficial in that NFC allows power transfer of an NFC tag (or antenna) to enable communication using a constant carrier signal. The WLC specification extends this communication functionality of NFC technology to enable wireless charging.

The WLC specification enables a safe charging process between two NFC-enabled devices in either static or negotiated modes. The static mode uses standard radio frequency (RF) field strength and provides a consistent power level. The negotiated mode uses a higher RF field supporting four power transfer classes of 250, 500, 750 and 1000 milliwatts. An on-board NFC module on the electronic device 100 can thus support different modes and in turn allow the battery 210 to be charged via a compatible NFC-enabled smartphone, charger, or other devices. Conserving battery power and efficiently using battery power in order to extend the running time of the electronic device 100 can involve a number of different approaches and/or compromises. For example, the screen in the top portion 102 can have display modes that differ depending on how the electronic device 100 is configured. In some implementations, to optimize overall energy efficiency, the second PCB 208 including sensors incorporates low power signal acquisition for the sensors.

In some implementations, the electronic device 100 includes the side touch track 220 provided on the exterior of one of the sidewalls of the electronic device 100. The side touch track 220 can provide a user interface for the user to interact with the electronic device 100. The side touch track 220 can sense touch signals (e.g., from the user's finger) and/or display state information related to the operation of electronic device 100, such as battery status/fuel gauge, sensor status, device status, wireless connectivity status, etc. Other information, such as health metrics, notifications, and alarms, can also be displayed on the side touch track 220. The behavior of the side touch track 220 may vary depending on how the electronic device is configured. For example, depending on the sensors included in the electronic device 100 on the first PCB 206 and/or the second PCB 208, some status information may be available and others not available. Depending on the electronic device 100 being configured as a smartwatch or a smart patch, some status information may be available and others not available. In some implementations, a lower cost model of the electronic device 100 with a smaller number of sensors can have more limited state information displayed compared to a higher cost model of the electronic device 100. In some implementations, apart from being part of the user interface of the electronic device 100, the side touch track 220 includes additional functionality, such as a biometric sensor (e.g., to enable fingerprint recognition), ECG measurements, or a flashlight mode (e.g., the side touch track 220 integrates light emitters for illuminating a dark environment).

Referring to FIG. 3, a bottom view of a first design 100a of the electronic device 100 of FIGS. 1 and 2 is provided, according to some implementations of the present disclosure. For convention, "100" in 100a refers to the electronic device 100 of FIGS. 1 and 2, and "a" indicates a first arrangement or design of the bottom of the electronic device 100. The first design 100a includes at least one connecting member 224. The connecting member 224 can be a snap connector (e.g., having a cavity for receiving a counterpart connecting member). The connecting member 224 is shown to have a circular shape, but other shapes (e.g., a square, an oval, a polygon, etc.) can be used. FIG. 3 provides four connecting members 224 as an example, but in other embodiments, there can be less than four connecting members (e.g., two or three) or more than four connecting members (e.g., five, six, ten, etc.).

In some implementations, the first design 100a of the electronic device 100 includes at least one coupling element 302. The coupling element 302 can be a magnet for coupling the electronic device 100 to a surface. In some implementations, the coupling element 302 includes materials that can be magnetized either permanently or temporarily (e.g., metal). The coupling elements 302 can be rectangular, arched, circular, or polygonal members. FIG. 3 provides an example of the coupling elements 302 being four arched members. The number four is merely used as an example, that is, more than four or less than four coupling elements 302 can be provided. The coupling elements 302 are arranged in a circular configuration, separated by the connecting members 224. The coupling elements 302 and the connecting members 224 are arranged around a perimeter of the housing window 222. In some instances, the shape of the housing window 222 dictates the shape of the arrangement of the connecting members 224 and the coupling elements 302. In some instances, the shape of the arrangement of the connecting members 224 and the coupling elements 302 dictates the shape of the housing window 222. In FIG. 3, the circular housing window 222 results in a circular arrangement of the connecting members 224 and the coupling elements 302. The arrangement is symmetric about the perimeter of the housing window 222. In some implementations, the first design 100a of the electronic device 100 includes one or more lateral electrodes 304. The lateral electrodes 304 can be placed next to the connecting members 224 as depicted in FIG. 3. The lateral electrodes 304 can be bioimpedance electrodes. In some implementations, part of the side touch track 220 is visible from the bottom view.

In some embodiments, the first design 100a of the bottom of the electronic device 100 facilitates transforming the electronic device 100 from a smartwatch configuration to a smart patch configuration using the coupling elements 302 as part of a locking system. The coupling elements 302 can include magnets, thus the electronic device 100 can have a magnetic lock system. When converting from the smartwatch to the smart patch, the connecting members 224 can have a shape that matches one or more of the electrode connectors on an adhesive patch. When in the smart patch mode, the connecting members 224 and the lateral electrodes 304 can be used for either ECG measurements, bioimpedance measurements, or both. In some implementations, at least two connecting members 224 are ECG electrodes. Symmetric distribution of the connecting members 224 can help provide more accurate health-related data avoiding signal crosstalk. In some implementations, symmetric distribution of the connecting members 224 help firmly attach the bottom of the electronic device 100 to the adhesive patch.

Distribution of the connecting members 224 (or in some cases ECG electrodes) and/or the lateral electrodes 304 (or bioimpedance sensors), as well as the location of any other sensor in the electronic device 100, can be configured in any number of ways so as to adapt to different external data extraction techniques. Each connecting member 224 is electrically insulated from an adjacent connecting member 224 by the housing of the electronic device 100, thus, avoiding any interference of the signals between the connecting members 224 and/or the lateral electrodes 304. In an example, the connecting members 224 are electrodes in contact with snap electrode buttons that facilitate connecting the connecting member 224 to the adhesive patch. The snap electrode buttons include conductive materials, e.g., silver or silver chloride.

Figure 4:
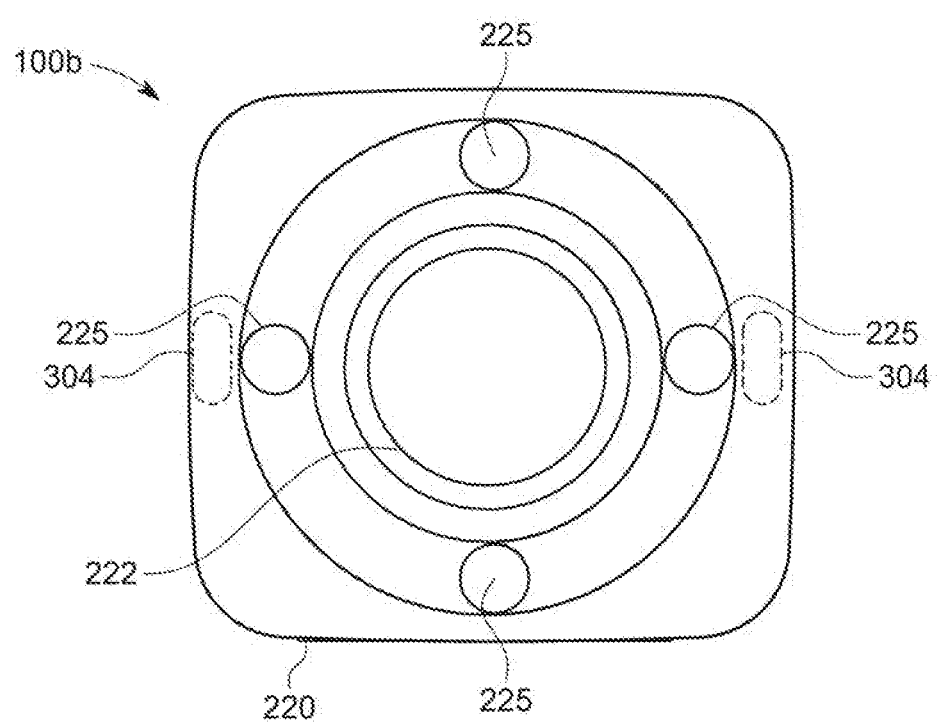
FIG. 4 illustrates a bottom view of a second design of the electronic device of FIG. 1, according to some implementations of the present disclosure.

Referring to FIG. 4, a bottom view of a second design 100b of the electronic device 100 of FIGS. 1 and 2 is provided, according to some implementations of the present disclosure. The second design 100b of the electronic device 100 includes connecting members 225 that are received at the adhesive patch. The connecting members 225 are shown to have a flat surface. Compared to the first design 100a of FIG. 3, the second design 100b does not include the coupling elements 302. Thus, the connecting members 225 are shown in FIG. 4 as flat connectors, but in other embodiments can be snap connectors. In such embodiments where the connecting members 225 are snap connectors, the connecting members 225 can be relied upon as the primary locking mechanism to secure the electronic device 100 to the adhesive patch. Flat electrodes can be desirable when contacting directly the skin of the user.

Figure 5:
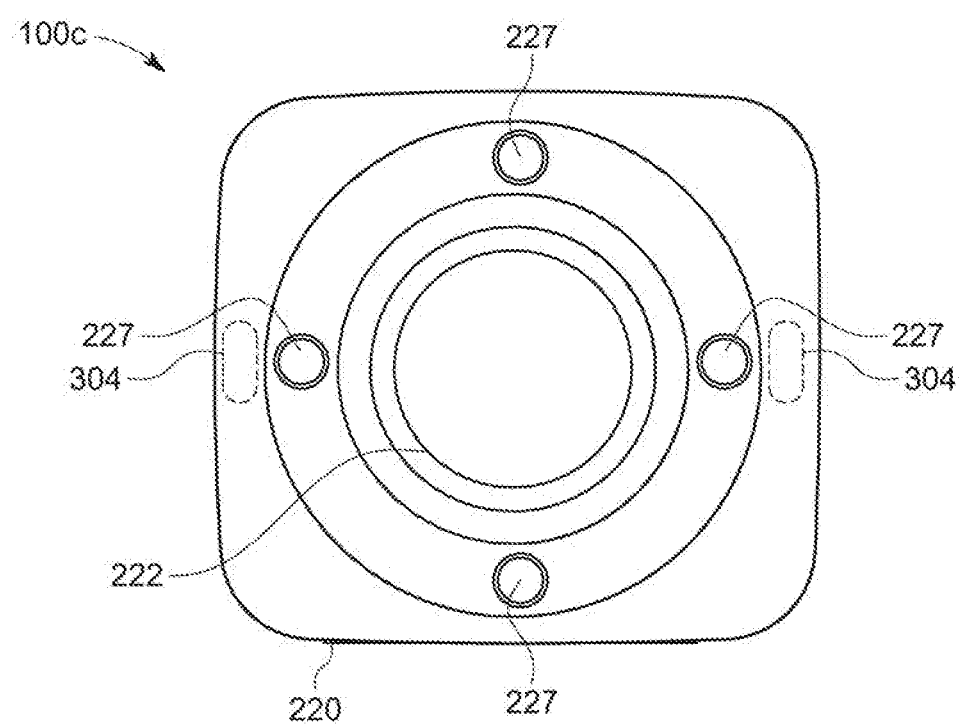
FIG. 5 illustrates a bottom view of a third design of the electronic device of FIG. 1, according to some implementations of the present disclosure.

Referring to FIG. 5, a bottom view of a third design 100c of the electronic device 100 of FIGS. 1 and 2 is provided, according to some implementations of the present disclosure. The third design 100c is similar to the second design 100b of FIG. 4, except the third design 100c includes connecting members 227. The connecting members 227 are shown in FIG. 5 as snap connectors. Similar to the connecting member 224 and 225, other design choices regarding snap or flat connectors can be made. The electronic device 100 with the third design 100c can be made specifically for being received in a patch housing as will be discussed later in some implementations of the present disclosure.

The lateral electrodes 304 in FIGS. 3, 4 and 5 can be a constant current source and high input impedance. In each of FIGS. 3, 4, and 5, each of the lateral electrodes 304 are used in conjunction with an aligned connecting member (e.g., the connecting member 224, 225, 227) forming a tetrapolar electrode configuration. The lateral electrodes 304 and the aligned connecting member may be multiplexed with ECG or electrodermal activity (EDA) sensors. The shape of the lateral electrodes 304 can vary in different embodiments as the contact area and electrical characteristics control the depth and precision of readings made from the lateral electrodes 304. Furthermore, electrode interference artifacts and overall impedance errors are reduced when arranging a tetrapolar system with two stimulant lateral electrodes 304 and two aligned connecting members to obtain measurements, thus providing a uniform current density distribution in the area of the user's body being analyzed.

Figure 6:
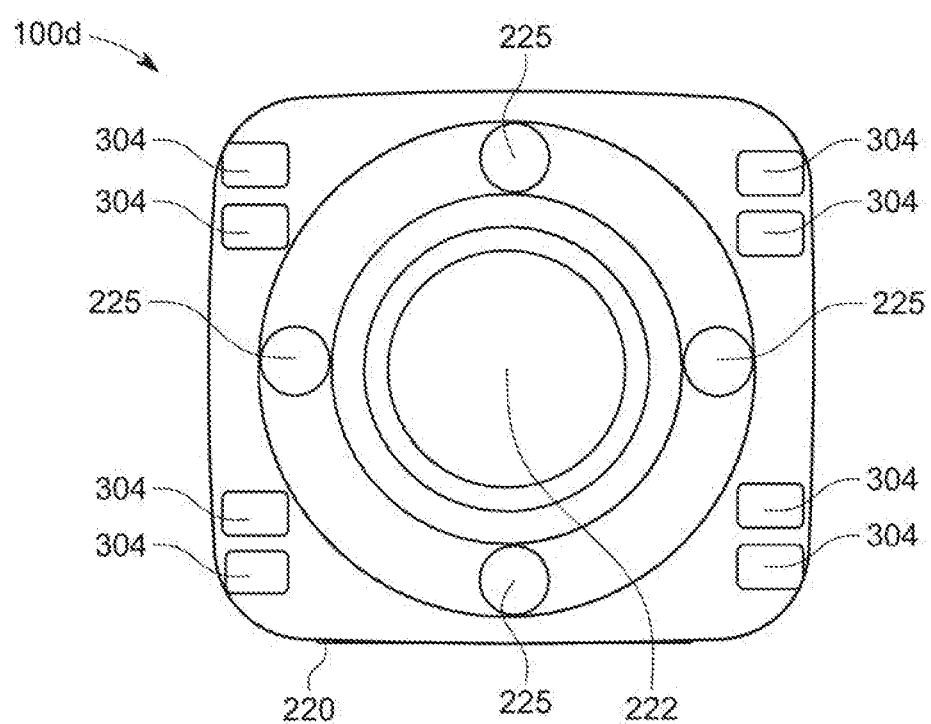
FIG. 6 illustrates a bottom view of a fourth design of the electronic device of FIG. 1, according to some implementations of the present disclosure.

Referring to FIG. 6, a bottom view of a fourth design 100d of the electronic device 100 of FIGS. 1 and 2 is provided, according to some implementations of the present disclosure. The fourth design 100d is different from the second design 100b in that the fourth design 100d includes eight lateral electrodes 304 that are not aligned with the connecting members 225. Four lateral electrodes 304 are provided on the left side of the fourth design 100d, and four lateral electrodes 304 are provided on the right side of the fourth design 100d. In some implementations, the arrangement of the lateral electrodes 304 in FIG. 6 provides two sources of bioimpedance signals, which can increase accuracy of bioimpedance measurement compared to the arrangements in FIG. 3, 4, or 5. In FIG. 6, a differential reading can be performed whereby a difference between the four lateral electrodes 304 on the left and the four lateral electrodes 304 on the right represent a combined impedance of skin and subcutaneous tissue at one or more sites on the user.

Figure 7:
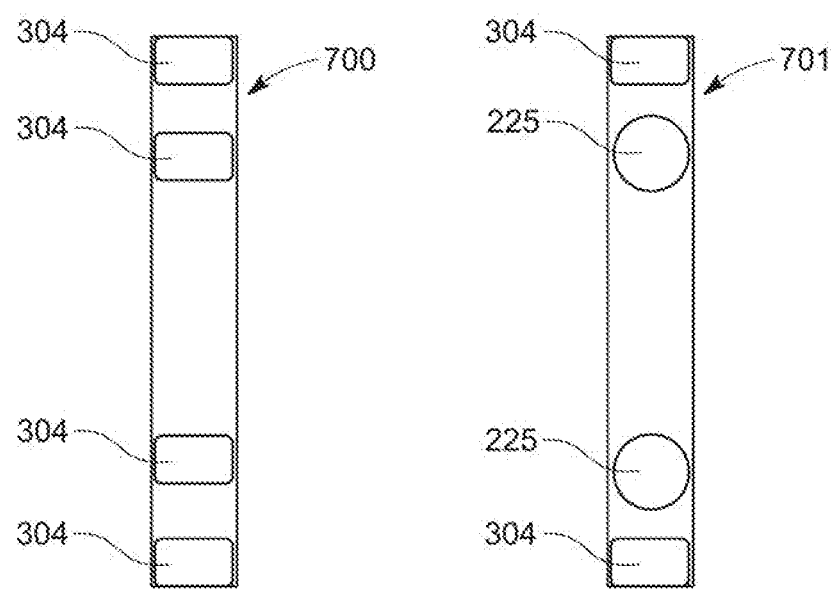
FIG. 7 illustrates a summary of possible four-electrode layouts for bioimpedance acquisition based on FIGS. 3-6, according to some implementations of the present disclosure.

FIG. 7 illustrates a summary of possible four-electrode layouts for bioimpedance acquisition, according to some implementations of the present disclosure. A first four-electrode layout 700 is similar to the arrangement of the lateral electrodes 304 in FIG. 6. A second four-electrode layout 701 is similar to the arrangement of the lateral electrodes 304 and aligned connecting members (e.g., the connecting member 224, 225, or 227) in FIGS. 3, 4 and 5. Four-electrode layouts 700 and 701 provide a set for measuring bioimpedance in some implementations of the present disclosure. Spacing between electrodes and/or connecting members can be chosen to achieve desired depths and sensitivity in tissue. Both of the four-electrode layouts 700 and 701 present a smaller distance between stimulating and measuring electrodes, since increasing the distance between electrode pairs would lead to a decrease in the magnitude of the measured impedance. In the layouts 700 and 701, the stimulating electrodes are on the extremes and the measuring electrodes are arranged in between. For example, in the layout 701, the connecting members 304 are stimulating electrodes, and the connecting members 225 are measuring electrodes.

Figure 8:
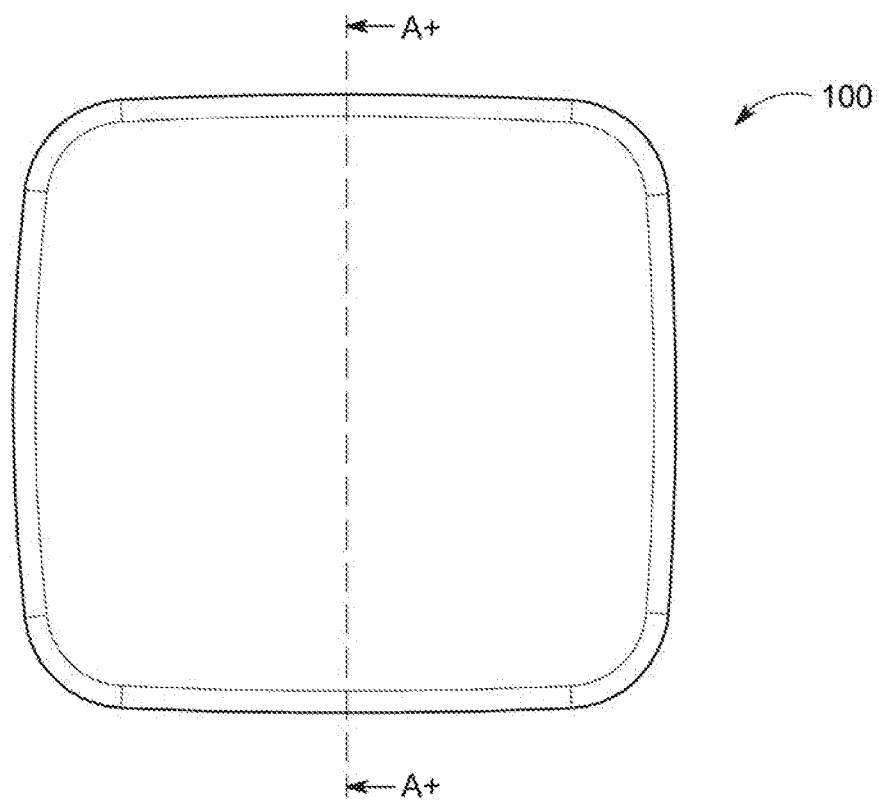
FIG. 8 illustrates a cross-sectional view of the electronic device of FIG. 1, according to some implementations of the present disclosure.
Figure 8:
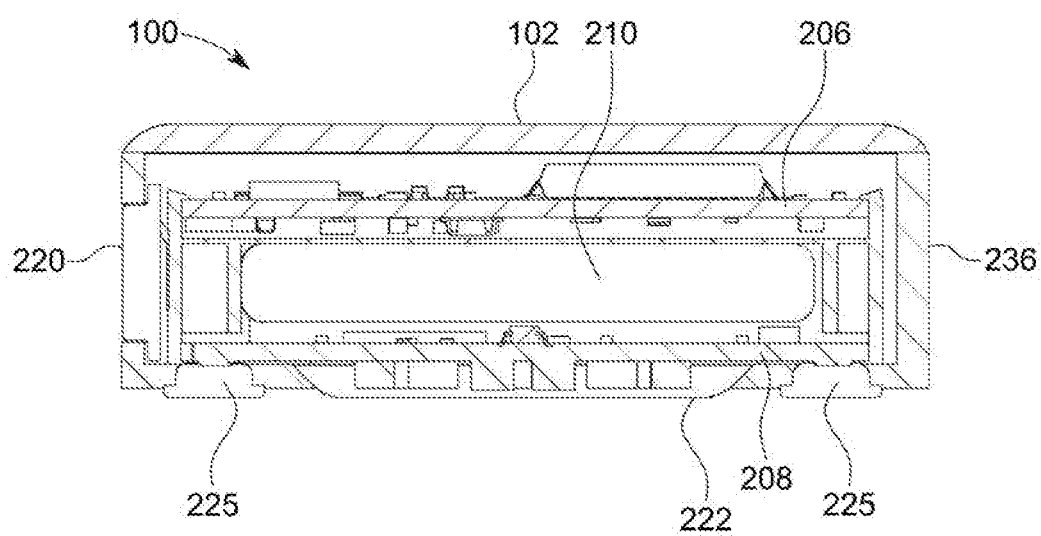

FIG. 8 illustrates a cross-sectional view of the electronic device 100 of FIG. 1, according to some implementations of the present disclosure. In some implementations, the cross-sectional view along the section denoted as A+-A+ is based on the second design 100b (FIG. 4). The connecting member 225 is shown as a flat connector that is leveled with the housing window 222. FIG. 8 also illustrates a position of the side touch track 220.

Increasing proximity of the housing window 222 to sensors on the second PCB 208 can enhance accuracy of data acquisition. In some implementations, sensors on the second PCB 208 are less than about 0.33 mm from the housing window 222. The housing window 222 protects the sensors from external particles and other conditions that could damage the sensors and/or affect accuracy of data acquisition. The height of the electronic device 100 can be reduced along with the overall size of the enclosed chamber, by decreasing the thickness of the battery 210. In some implementations, the overall size of the enclosed chamber can be reduced by using other types of batteries (e.g., a thin film Lithium battery, which allows a simple constant-voltage recharge with no current limiting required; a solid-state, flexible, rechargeable, thin-film micro-energy cell (MEC); etc.). In some implementations, for radiation purposes, the battery 210 may be shielded to reduce and/or avoid leakage of radio frequency (RF) radiation towards the user.

Figure 9A:
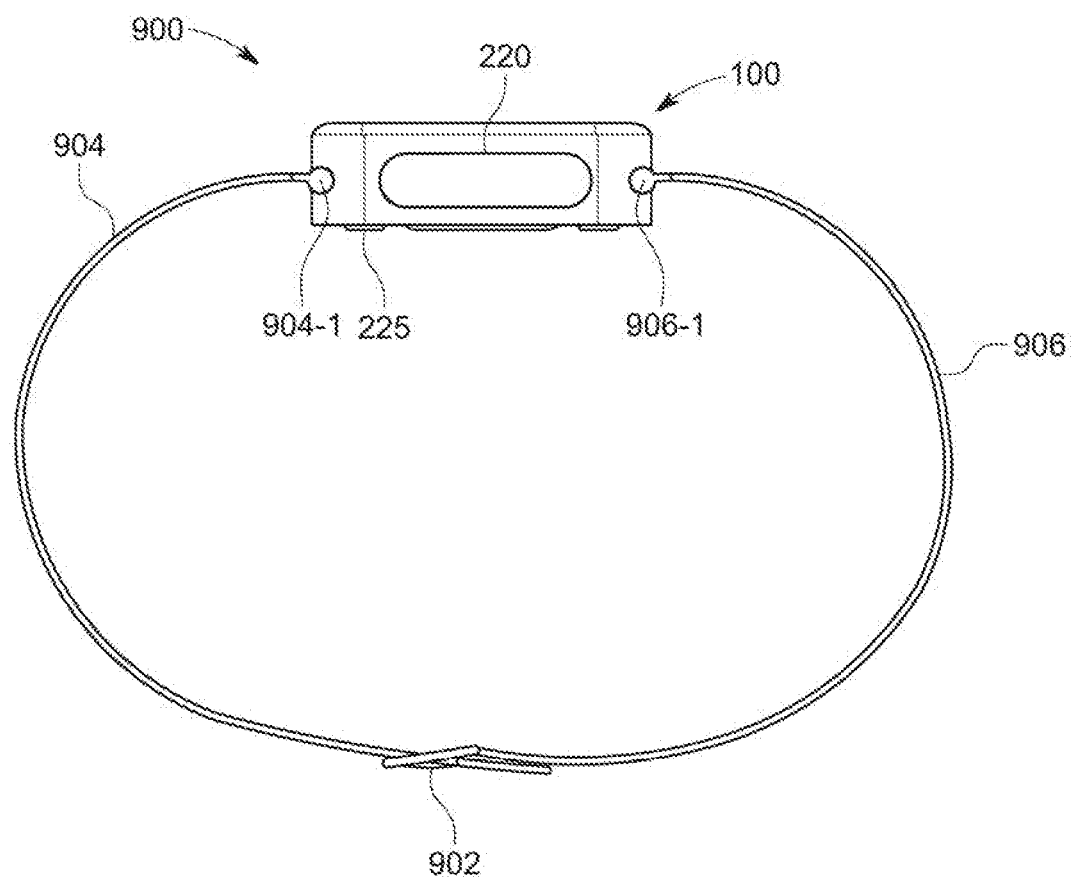
FIG. 9A illustrates a side view of the electronic device of FIG. 1 in a smartwatch configuration, according to some implementations of the present disclosure.
Figure 9B:
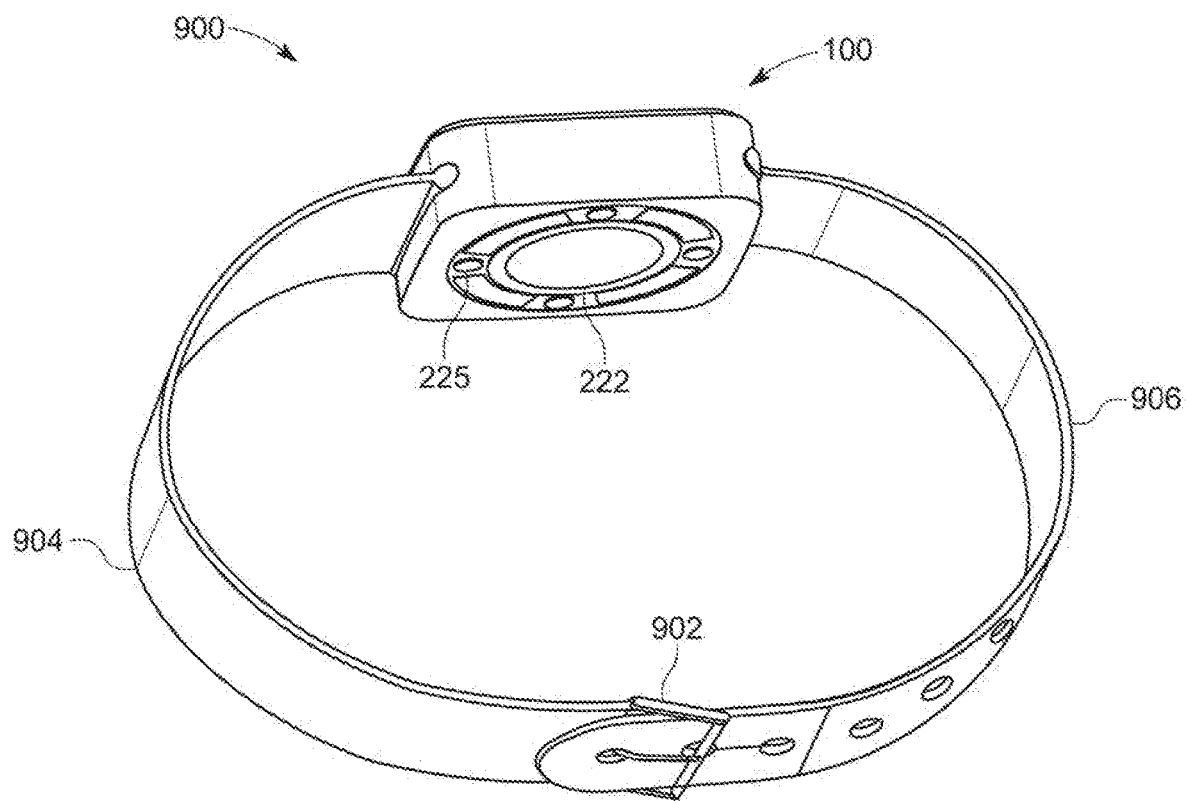
FIG. 9B illustrates a bottom perspective view of the electronic device of FIG. 9A.

The electronic device 100 can be adorned in multiple manners. For example, straps, bands or adhesive patches can be used with the electronic device 100 to secure the electronic device 100 to a body part of the user. Referring to FIG. 9A, a side view of a smartwatch configuration 900 of the electronic device 100 is provided, according to some implementations of the present disclosure. FIG. 9B illustrates a bottom perspective view of the smartwatch configuration 900 of FIG. 9A. The smartwatch configuration 900 allows the electronic device 100 to be wearable on a wrist of the user. When adorned on the wrist of the user, the electronic device 100 includes the connective members 225 at least partially touching the wrist of the user while the screen on the top portion 102 (FIG. 2) of the electronic device 100 faces up. The smartwatch configuration 900 includes bands or straps 904, 906 that couple with the electronic device 100. A connective end 904-1 of the strap 904 engages one side of the electronic device 100 and a connective end 906-1 of the strap 906 engages an opposite side of the electronic device 100. The strap 904 is coupled to the strap 906 using a buckle 902. The strap configuration described is merely provided as an example. In some implementations, only one strap with two connective ends is needed. In some implementations, the one strap has elastic properties so as to stretch when the user adorns or removes the smartwatch from the user's wrist. The bottom perspective view in FIG. 9B is merely provided as an example. The electronic device 100 can have electrode and/or magnet arrangements according to any of the first, second, third, fourth designs as described in connection with FIGS. 3-6.

Figure 9C:
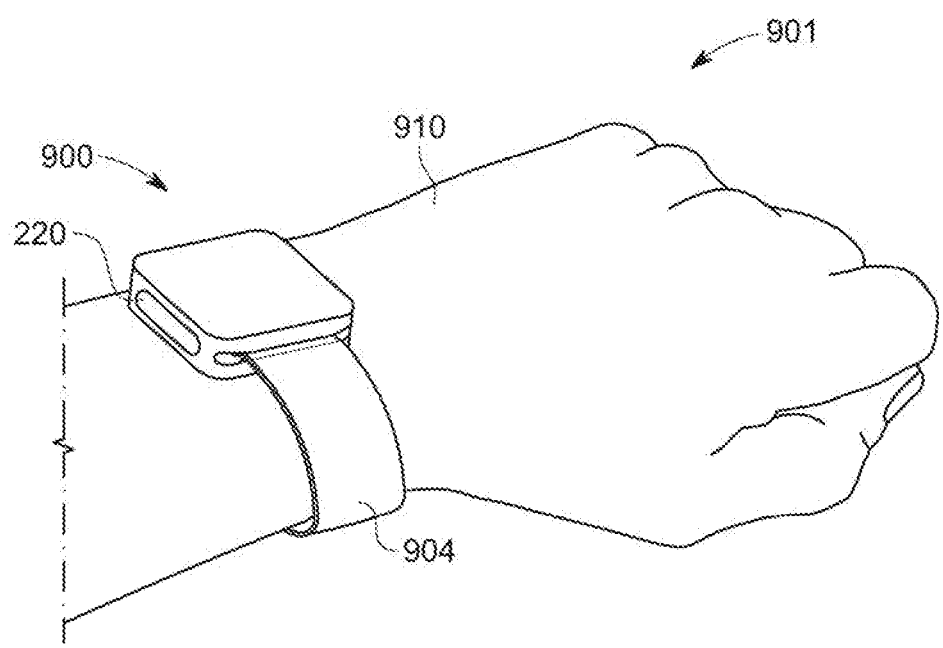
FIG. 9C illustrates a perspective view of the electronic device of FIG. 9A while on a wrist of a user, according to some implementations of the present disclosure.

Each of the straps 904, 906 can be a piece of elastic fabric, metal, leather or a modular concept with one or various links to adjust the fit of the straps 904, 906 to the wrist of the user as illustrated in FIG. 9C. FIG. 9C illustrates a perspective view of a combination 901 that includes the user's hand 910 and the smartwatch configuration 900. FIG. 9C is merely provided as an example. The electronic device 100 can be integrated in bracelets. The buckle 902 in FIGS. 9A and 9B can be replaced with other securing methods (e.g., a plug fit method, a clasping method, etc.). The buckle 902 can support a wide fitting range by providing multiple adjustment levels. The strap 906 is shown to include multiple adjustment holes in FIG. 9B that match a buckle tongue of the strap 904. There are similarly other adapting mechanisms contemplated as twistable and expandable elastic mesh/textiles from carbon fiber, to nylon and cotton. The straps 904, 906 can have various optional fixed sizes to be wearable over different users' wrists.

In some implementations, the straps 904, 906 can include electronic components and sensors embedded in a flexible circuit board to enable watchband monitoring of health metrics and adjust settings. The straps 904, 906 can provide personalized cooling/heating, sweat analysis sensors, subcutaneous interstitial fluid sensors (e.g., for glucose measurement), electrodes for measuring bioimpedance, a microneedle array for automated subcutaneous delivery of drugs/treatments (e.g., insulin), etc. The straps 904, 906 can have a soft and stretchy composition that can be used for cooling or warming the skin of the user to a comfortable temperature. Once at the target temperature, the straps 904, 906 can be used to maintain the skin temperature as the ambient temperature changes. As such, the straps 904, 906 can incorporate a thermo-regulating function. In some implementations, the straps 904, 906 can be automatically adjusted such that tightness of the straps 904, 906 can vary based on a relative position of the electronic device 100 when strapped to the wrist of the user. The position of the electronic device 100 can be provided by proximity sensors included in the electronic device 100. The proximity sensors can be provided on the second PCB 208 (FIG. 8) for sensing, through the housing window 222, the relative positioning of the electronic device 100 and the skin of the user. Automatically adjusting the straps 904, 906 improves accuracy of sensor readings by allowing the connecting members 225 (FIG. 9B) to remain in contact with the skin of the user. In some implementations, a thermo-regulating strap, an automatic adjusting strap or any other electronics embedded in a strap are powered by a flexible, stretchable battery pack that can be embedded, and charged from the electronic device 100 or a separate charging source.

In some implementations, the electronic device 100 is waterproof or water-sealed. Thus, the straps 904, 906 can be high-quality rubber that enables waterproof and easy clean care. The buckle 902 can be stainless steel, meeting the water-resistant and/or waterproof requirement. In some implementations, micro-perforated sweat-resistant lining to anti-allergic and durable reinforced microfibrillar material is used for the straps 904, 906.

In some implementations, the smartwatch configuration 900 prioritizes certain sensors within the electronic device 100. For example, the electronic device 100 can prioritize a camera, a microphone array, speakers, haptic feedback, and/or other standard smartwatch features. The microphone array may support beamforming, adaptive steering, active noise cancellation, sound amplification and other signal processing techniques for capturing voice input and/or high-quality biological sounds from the user's body when the electronic device 100 is attached to the user. In some implementations, the microphone array is positioned at the bottom of the electronic device 100 (e.g., on the second PCB 208 of FIG. 2, at a location on the exterior of the bottom portion of the electronic device 100, etc.) in order to capture biological sounds. In some implementations, the microphone array is positioned elsewhere to facilitate voice input (e.g., on one of the sidewalls 236 of FIG. 2).

In some implementations, the side touch track 220 (FIG. 9A) in the smartwatch configuration 900 is configured as an ECG electrode. When adorned on the wrist of the user, the connecting members 225 are in contact with the wrist of the user to provide one contact with the user. When the user touches the side touch track electrode 220 with a finger from the opposite hand, the side touch track 220 can function as another contact location with the user, thus forming a complete ECG signal circuit for obtaining lead I ECG readings. The side touch track 220 can be connected to the second PCB 208 (the sensor PCB) or can be connected to the first PCB 206. The first PCB 206 and/or the second PCB 208 of FIG. 2 can analyze, process, or communicate the obtained ECG data. The analyzed or processed ECG data can be sent to other computing devices or raw ECG data can be sent to other computing devices. In some implementations, at least a portion of the side touch track 220 includes a conductive material to facilitate the side touch track 220 functioning as an ECG electrode. The conductive material can include metals, metal alloys, or liquid metal. In some implementations, the ECG electrode is placed adjacent to the side touch track 220 or on an opposite sidewall 236 (FIG. 2) not containing the side touch track 220.

Figure 10B:
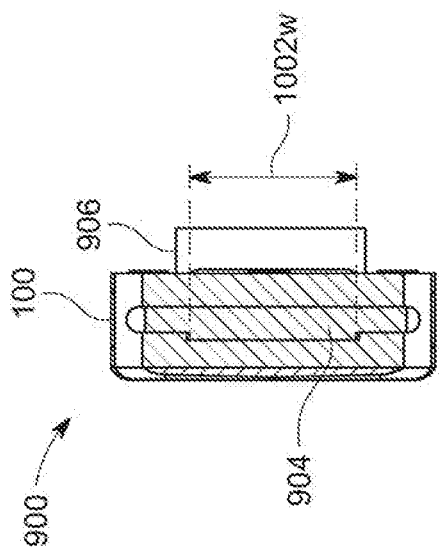
FIG. 10B illustrates a first cross-sectional view of the electronic device of FIG. 10A, according to some implementations of the present disclosure.
Figure 10D:
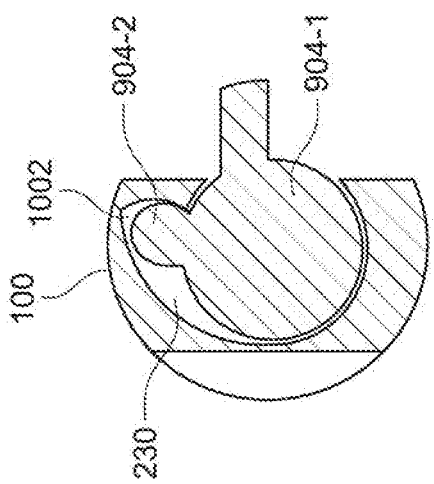
FIG. 10D illustrates a strap-locking mechanism for the electronic device of FIG. 10A, according to some implementations of the present disclosure.
Figure 10A:
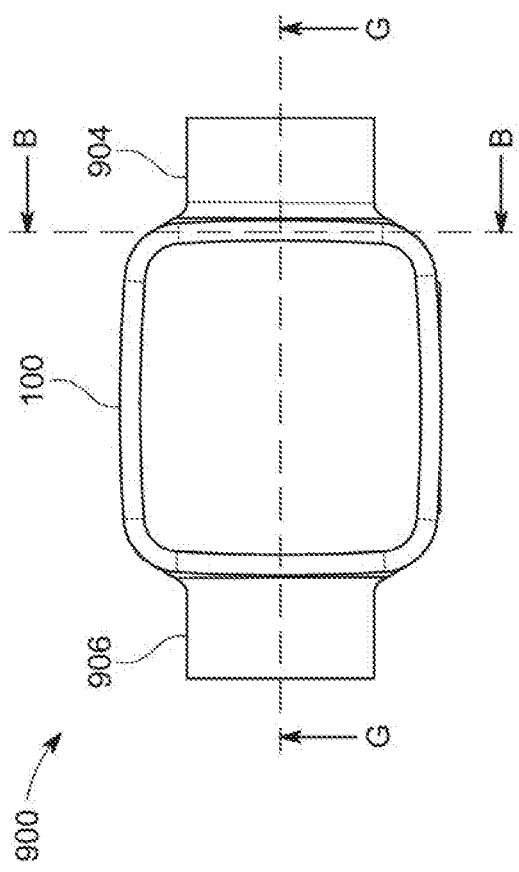
FIG. 10A illustrates a top plan view of the electronic device of FIG. 9A, according to some implementations of the present disclosure.
Figure 10C:
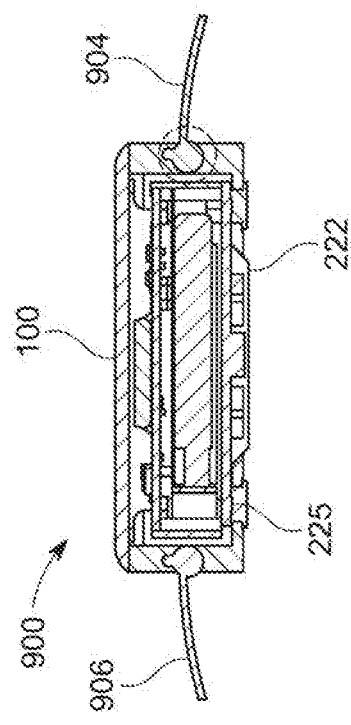
FIG. 10C illustrates a second cross-sectional view of the electronic device of FIG. 10A, according to some implementations of the present disclosure.

Referring to FIG. 10A, a top plan view of the smartwatch configuration 900 is illustrated, according to some implementations of the present disclosure. Two cutting plane lines B-B and G-G are illustrated in the top plan view. FIG. 10B illustrates a cross-section of the smartwatch configuration 900 along the cutting plane line B-B, and FIG. 10C illustrates a cross-section of the smartwatch configuration 900 along the cutting plane line G-G. FIG. 10D illustrates a zoomed in portion H of the locking mechanism identified in FIG. 10C. The cutting plane lines B-B and G-G provide additional details of lateral grooves (e.g., the groove 230) for connecting the straps 904, 906.

In FIG. 10B, a width and length of the groove 230 can be discerned. The groove 230 can include a central width expansion along the center of the groove 230 for locking the strap 904 to the electronic device 100. The central width expansion is referred to as a notch 1002, herein, in the disclosure. The groove 230 is shaped such that a top region of the groove 230 forms the notch 1002. In some implementations, the notch 1002 is positioned to receive a tab 904-2 situated on the connective end 904-1 of the strap 904. In some implementations, the tab 904-2 is a semi-rigid tab that enables the strap 904 to be centered in the groove 230. The semi-rigid tab can be a rubber tab, a silicone tab, a plastic tab, a resin tab, etc. An interaction of the semi-rigid tab with the notch 1002 prevents lateral displacement of the strap 904 along the groove 230 while the strap 904 is attached to the electronic device 100 in the smartwatch configuration 900. In FIG. 10D, the groove 230 is gradually enlarged to provide the notch 1002. The gradual groove enlargement towards the upper side of the groove 230 to create the notch 1002 allows a rotational lock where the strap 904 is locked in place when angled downwards and/or horizontally with respect to the horizontal plane of the electronic device 100. An arc length of the groove 230 from the perspective of FIG. 10D is about a tenth of the length of the groove 230 (length of the groove 230 can be discerned in FIG. 10B). In some implementations, the tab 904-2 is a rigid tab that can partially recess into the connective end 904-1. For example, the connective end 904-1 can include a spring mechanism that mechanically biases the tab 904-2 to protrude from the connective end 904-1 when fully within the notch 1002. When the strap 904 is rotated such that the tab 904-2 travels counterclockwise along the groove 230 as shown in FIG. 10, the tab 904-2 can be pushed into or can recede into the connective end 904-1. The spring mechanism can allow the rigid tab to recede into the connective end 904-1 when the tab 904-2 is not within the notch 1002. The spring mechanism can allow the rigid tab to fully protrude from the connective end 904-1 when the tab 904-2 is within the notch 1002. Whether with a semi-rigid tab or a mechanically biased tab, the strap 904 can engage and disengage from the electronic device 100 at the location of the groove 230.

Figure 11A:
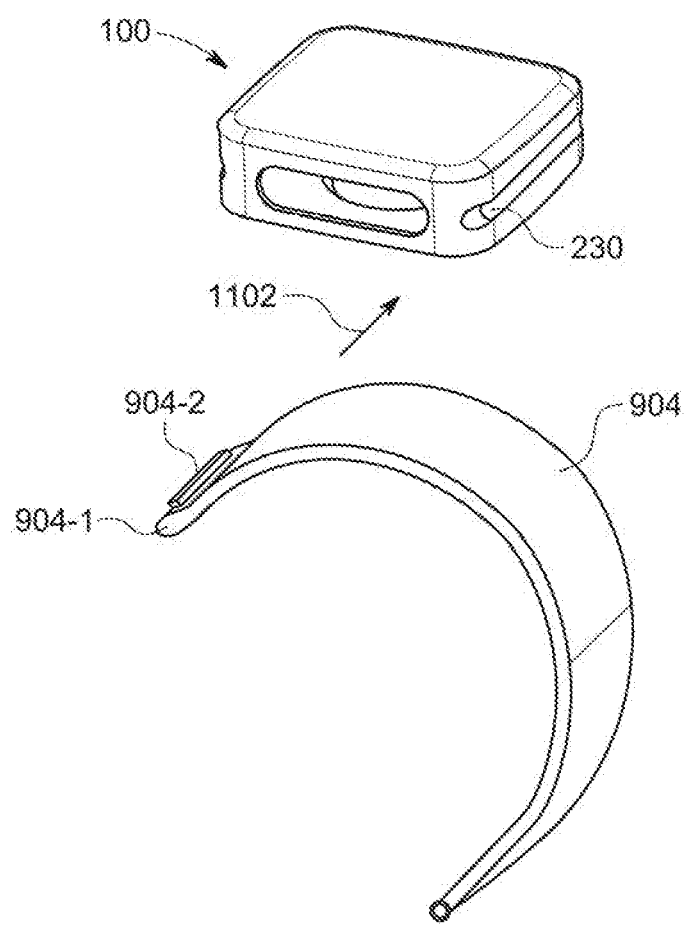
FIG. 11A illustrates a first step in attaching a strap to the electronic device of FIG. 1, according to some implementations of the present disclosure.
Figure 11B:
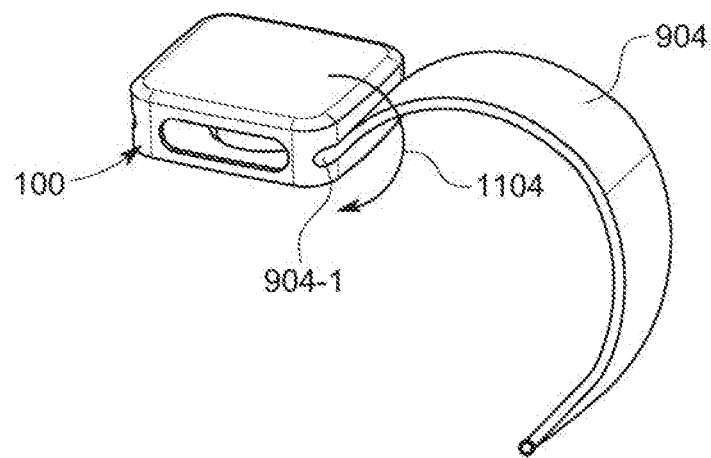
FIG. 11B illustrates a second step in attaching the strap in FIG. 11A to the electronic device of FIG. 1, according to some implementations of the present disclosure.
Figure 11C:
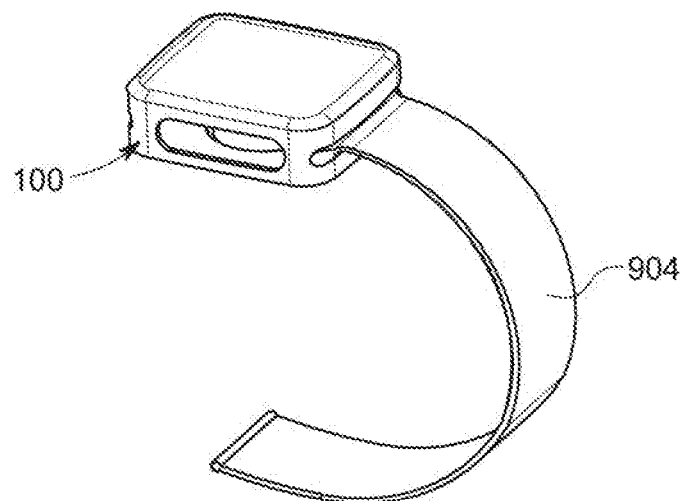
FIG. 11C illustrates the strap in FIG. 11A attached to the electronic device of FIG. 1, according to some implementations of the present disclosure.
Figure 11D:
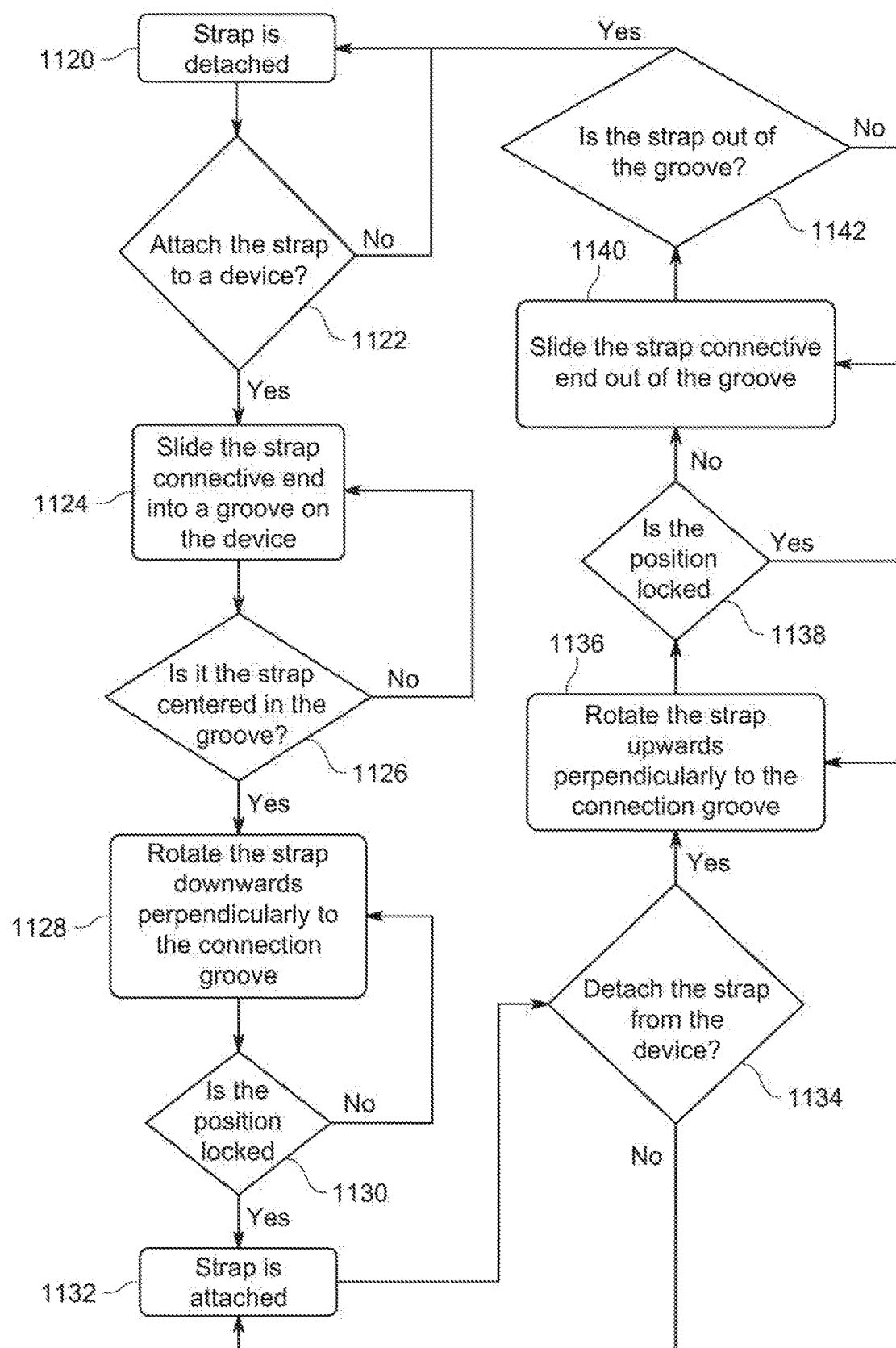
FIG. 11D is a flow chart illustrating a process for attaching and detaching a strap to a device, according to some implementations of the present disclosure.

Referring to FIG. 11A-D, a method of engaging and disengaging a strap (e.g., the strap 904 of FIG. 10C) is provided, according to some implementations of the present disclosure. FIGS. 11A to 11C illustrate specific time slices, and FIG. 11D provides a flow diagram for the method. Referring to FIG. 11D, step 1120 indicates that a status for a watch strap (e.g., a smartwatch's strap) is indicated as detached. An example of such a status is provided in FIG. 11A, where the electronic device 100 and the strap 904 are detached.

At step 1122, a decision on whether the watch strap should be attached to a device is determined. If the decision at step 1122 is a "no", then the strap stays detached from the device. If the decision at step 1122 is a "yes", then at step 1124, the connective end of the strap is slid into a groove provided on the device. For example, in FIG. 11A, if the strap 904 is to be connected to the electronic device 100, then the connective end 904-1 slides into the groove 230 in the direction 1102. The strap 904 is slightly angled to be received in the groove 230. The tab 904-2 is compressed when received in the groove 230 at the slightly angled position.

At step 1126, a determination is made whether the strap is centered in the groove. If the strap is not centered, then the strap is slid in the groove until centered. For example, referring to FIG. 10B a centered region $1002w$ of the groove 230 is where the notch 1002 (FIG. 10D) is provided. The length of the centered region $1002w$ is about 60 to 70 percent of the length of the groove 230. In some implementations, the groove is about 32 mm. In some implementations, the groove is between about 30 mm and 40 mm. These dimensions are merely provided as examples. Centering the strap 904 at the centered region $1002w$ will facilitate locking the strap 904 in the groove 230. At step 1128, when centered, the strap is rotated downwards, perpendicular to the groove. For example, in FIG. 11B, the connective end 904-1 of the centered strap 904 is rotated or pivoted within the groove in the direction 1104.

Step 1130 involves determining whether the position of the strap is locked. For example, referring to FIG. 10D, that is whether the tab 904-2 is positioned in the notch 1002 such that the tab 904-2 locks the strap 904 in place. If the strap 904 can continue rotating in the direction 1104 shown in FIG. 11B, then the tab 904-2 is not at a locking position and the strap 904 should be further rotated. If the strap 904 is in the locking position, then the strap is attached in step 1132. FIG. 11C provides an example of the strap 904 being in a locked position relative to the electronic device 100.

Steps 1134, 1136, 1138, 1140, and 1142 provide a reverse process of removing the strap from the device. At step 1134, when determined that the strap should be removed from the device, then at step 1136, the strap is rotated upwards perpendicularly to the connection groove. For example, the strap 904 is rotated in a direction opposite to that of the direction 1104 illustrated in FIG. 11B. A determination is made at step 1138 on whether the position of the strap is locked. For example, a determination is made whether the tab 904-2 in FIG. 10D is recessed or compressed against the groove 230 such that the connective end 904-1 can slide out of the groove 230.

If the position is locked at step 1138 (i.e., the tab 904-2 is not compressed or recessed against the groove), then the strap should continue to be rotated at step 1136. Otherwise, if the position is not locked, then at step 1140, the strap can be slid out of the groove in the device. For example, the strap 904 can be slid out of the groove 230 in the direction 1102 of FIG. 11A or in a direction opposite to that of 1102. That is, the connective end 904-1 can laterally slide out of the groove 230. The sliding continues until the determination is made at step 1142 that the strap is out of the groove.

Although rotation of the strap 904 is provided in the present disclosure, other alternatives like a pressure fit or a button lock can be used to attach the strap 904 to the electronic device 100. Although described in the context of connecting a watch strap to an electronic device, the locking mechanism disclosed herein can be used to mechanically couple any two objects together and is not limited herein to the example of a watch strap and an electronic device.

Figure 12:
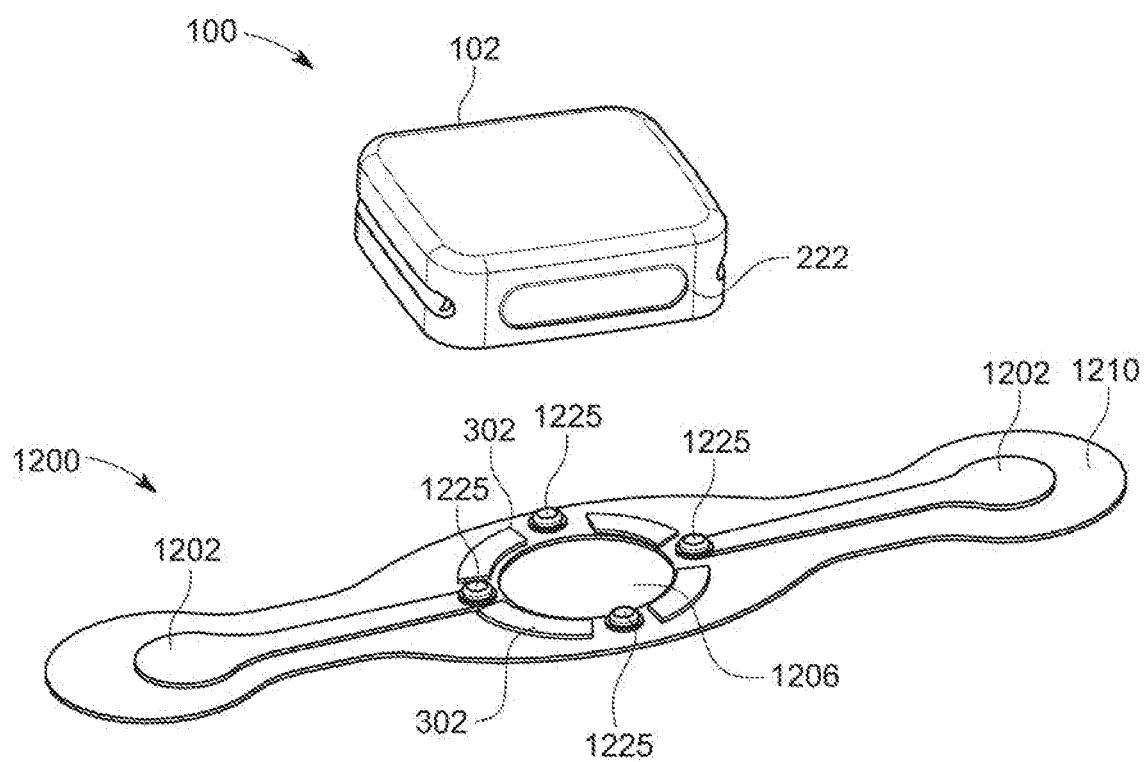
FIG. 12 illustrates example components of a smart patch, according to some implementations of the present disclosure.

FIGS. 9A-11D involved configuring the electronic device 100 of FIG. 1 in a smartwatch configuration (e.g., the smartwatch configuration 900). The electronic device 100 can be configured in a smart patch configuration. In a smartwatch configuration, the electronic device 100 can measure bioimpedance or other measurements on the wrist of the user using the connecting members 224, 225, or 227 of FIGS. 3-5, as discussed in connection with FIG. 7. In a smart patch configuration, the electronic device 100 can be affixed to the skin of the user on any body part of the user, thus allowing bioimpedance or other measurements using the connecting members 224, 225, or 227. FIG. 12 illustrates an example smart patch configuration of the electronic device 100, according to some implementations of the present disclosure. The smart patch configuration of FIG. 12 includes the electronic device 100 in a process of being coupled to a patch assembly 1200, where the combination of the electronic device 100 and the patch assembly 1200 is referred to as a smart patch. The patch assembly 1200 can be disposable.

Figure 13:
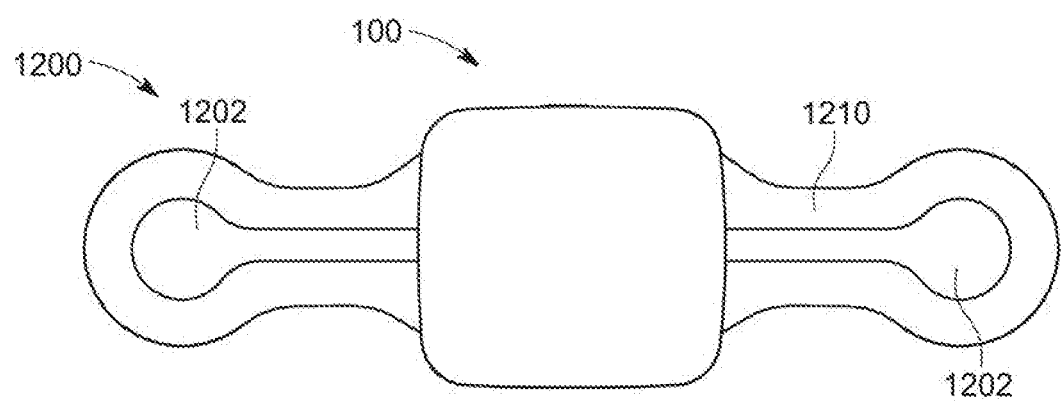
FIG. 13 illustrates a top plan view of the smart patch of FIG. 12.

In some implementations, the patch assembly 1200 includes a substrate with a first surface 1210 and a second surface (not shown) below the first surface 1210. The patch assembly 1200 includes one or more electrodes 1202. The electrodes 1202 can be ECG electrodes. The electrodes 1202 may be dry electrodes, wet electrodes (e.g., hydrogel), or semi-dry electrodes. The electrodes 1202 can be electrically and mechanically coupled to connecting members 1225 that can snap into a corresponding connecting member (e.g., the connecting member 224 of FIG. 3) on the electronic device 100. The electrodes 1202 can connect to the connecting members 1225 using a wire or flat conductive material (not shown). The connecting members 1225 are similar to connecting members already described in connection with various implementations of the present disclosure. The electrodes 1202 can make physical contact to the skin of the user through the second surface (not shown) of the substrate, and the connecting members 1225 are provided on the first surface 1210 of the substrate. The substrate can include additional connecting members 1225 not coupled to the electrodes 1202. The substrate can include one or more coupling elements 302. The coupling elements 302 can be magnets or metals as previously described in connection with FIG. 3. In some implementations, the coupling elements 302 are magnets that attract a metal component on the housing of the electronic device 100 such that the electronic device 100 is secured to the substrate. In some implementations, the coupling elements 302 are metal pieces that are magnetized by a magnet provided on the electronic device 100 such that the electronic device 100 is secured to the substrate. The electronic device 100 should be aligned such that corresponding coupling elements and/or corresponding connecting members on the electronic device 100 are coupled to the coupling elements 302 and the connecting members 1225. Although FIG. 12 provides an example where the connecting members 1225 are male snap connectors, other embodiments where the connecting members 1225 are female snap connectors or flat electrodes can be contemplated. The substrate further includes an opening 1206 to allow optical and/or other sensors provided on the electronic device 100 access to the skin of the user. Adhesive can be provided on the second surface of the substrate so that the substrate can be affixed to the skin of the user. FIG. 13 illustrates a top plan view of the smart patch of FIG. 12.

The smart patch of FIG. 12 can use a combination of skin-friendly materials with biocompatible substrates to achieve a thin, flexible, and elastic patch to be attached to the user. The substrate of the patch assembly 1200 can be made from thermoplastic polyurethane material (TPU), or variations of silicon and other elastic adhesives. The patch assembly 1200 has electronic functionality that includes electrodes 1202 and the connecting members 1225 to provide a stable and high-quality electrical connection to the user. Other electronics can be incorporated on the substrate of the second device 1200, e.g., strain gauges can generate data for monitoring breathing patterns of the user. The patch assembly 1200 solves a prior complexity issue from conventional electrodes where additional lead wires were used in contacting an electronic device.

In some implementations, different adhesive level options are provided for the second device 1200. Different patients may prefer different levels of adhesive (e.g., a high performance athlete or an older adult). That is, some adhesives can have a 24 hour, 48 hour, 72 hour, etc., wear time depending on user requirements and/or health and activity conditions (e.g., sweat, skin sensitivity, etc.). A standard adhesive can be recommended for over 72 hours. For the user, a disposable smart patch that can be worn for several days is more convenient and can reduce the waste of substrate material of the patch assembly 1200.

Figure 14:
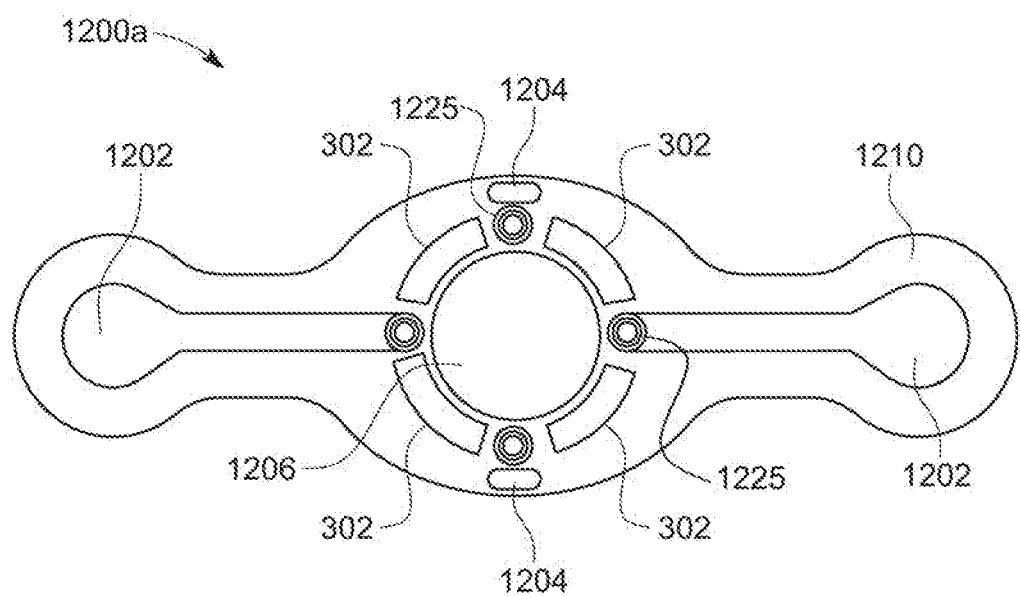
FIG. 14 illustrates a patch assembly, according to some implementations of the present disclosure.

Referring to FIG. 14, a patch assembly 1200a with a different arrangement of components compared to the patch assembly 1200 is provided, according to some implementations of the present disclosure. The patch assembly 1200a includes lateral portions 1204. In some implementations, the lateral portions 1204 are openings that provide access for lateral electrodes (e.g., the lateral electrodes 304 of FIG. 3) to interface with the skin of the user. In some implementations, the lateral portions 1204 are metal electrodes that make direct contact with the skin of the user from the bottom of the patch assembly 1200a, and conductively couple with lateral electrodes (e.g., the lateral electrodes 304 of FIG. 3) from the top of the patch assembly 1200a. In some implementations, the lateral portions 1204 and the electrodes 1202 may be one of dry electrodes, wet electrodes (e.g., hydrogel), or semi-dry electrodes. The patch assembly 1200a with the lateral portions 1204, electrodes 1202 and connecting members 1225 can be used with an electronic device (e.g., the electronic device 100) with a bottom design similar to or the same as the first design 100a of FIG. 3.

Figure 15:
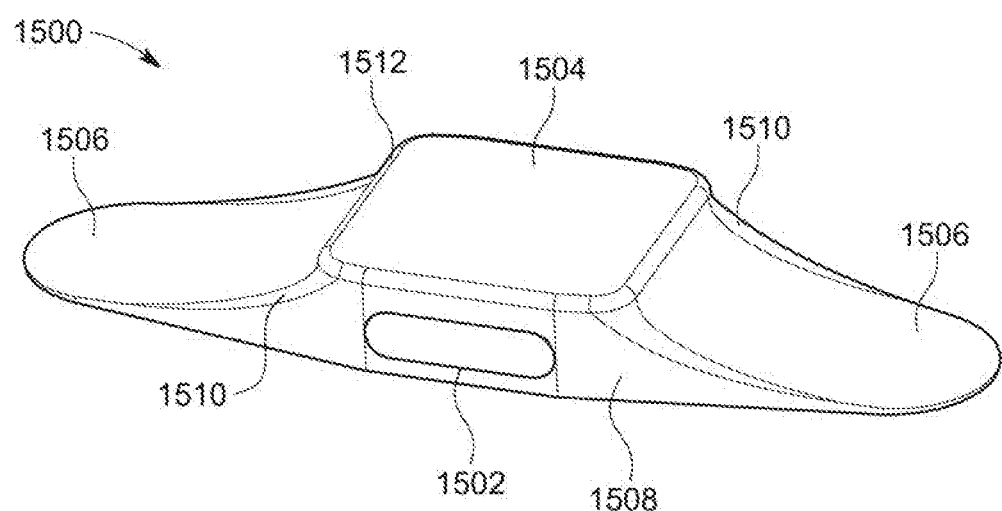
FIG. 15 illustrates a perspective view of a case body, according to some implementations of the present disclosure.

Referring to FIG. 15, a case body 1500 for use with a patch assembly is provided, according to some implementations of the present disclosure. The case body 1500 includes a top portion 1504, sidewalls 1506, 1508, and a side track window 1502. The top portion 1504 can cover the electronic device 100 to prevent light transmission from the screen of the electronic device 100. In some implementations, the top portion 1504 can be opaque, translucent or transparent for viewing the screen of the electronic device 100. The sidewalls 1508 can be vertical sidewalls, and the sidewalls 1506 can have a gradual incline to include a smooth curved surface. The smooth curved surface can be aesthetically pleasing and can promote comfort when affixed to the user. Smooth surfaces can prevent the user's clothing from interfering with the patch assembly. The case body 1500 can cover a patch assembly (e.g., the patch assembly 1200 of FIG. 12) and an electronic device (e.g., the electronic device 100 of FIG. 12). The case body 1500 can include smooth edges 1510, 1512. The smooth edges 1510, 1512 provide smooth transitions for the top portion 1504 and the sidewalls 1506, 1508. The side track window 1502 provides access to a side touch track (e.g., the side touch track 220 of FIG. 12). The side track window 1502 can be a translucent window (e.g., a plastic) that protects and provides access to the side touch track or can be an opening that provides direct access to the side touch track. In some implementations, a window similar to the side track window 1502 can be provided on the top portion 1504 to provide access to the screen of the electronic device 100.

Figure 16:
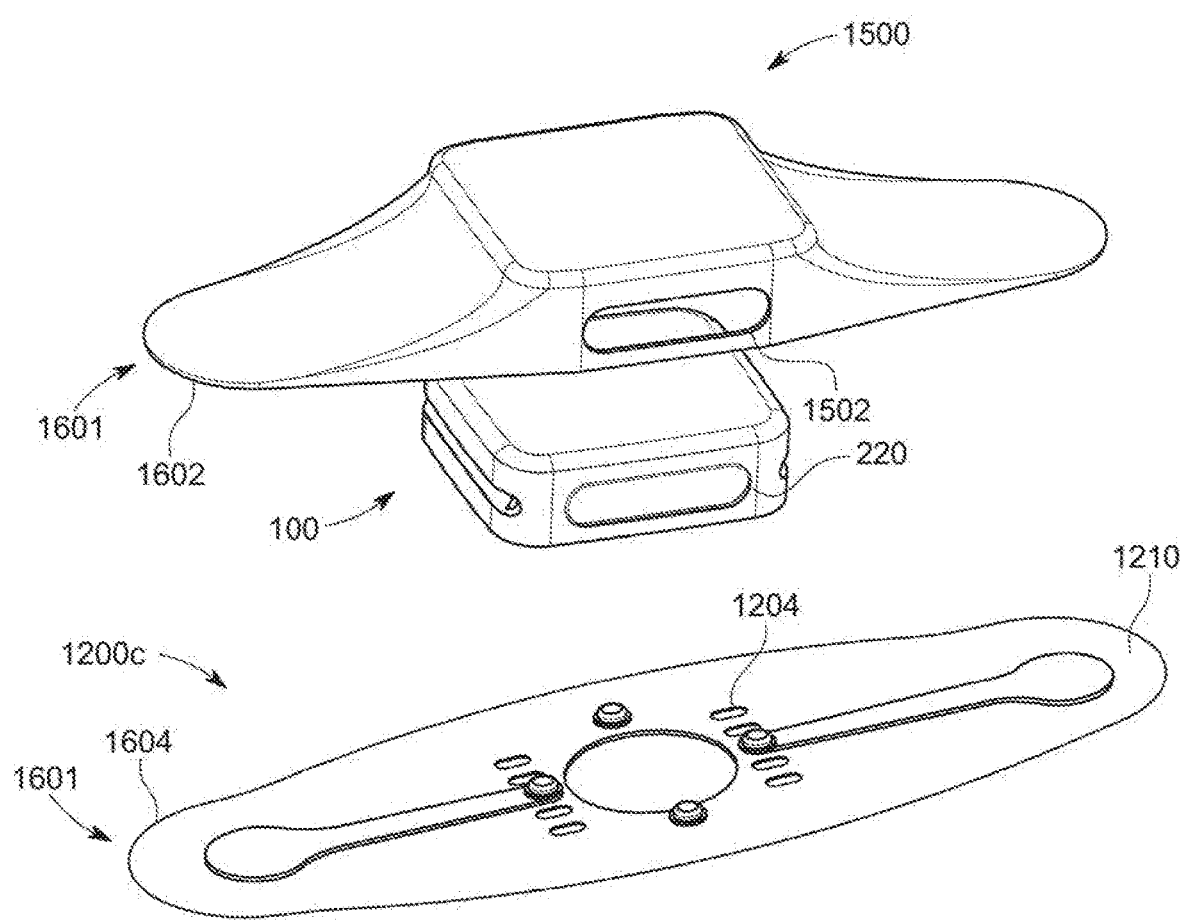
FIG. 16 illustrates an exploded view of components in a smart patch, according to some implementations of the present disclosure.

The case body 1500 does not have a bottom enclosure but lays atop or covers a patch assembly. A combination of a patch assembly (e.g., patch assembly 1200c of FIG. 16) and the case body 1500 is referred to as a patch housing. FIG. 16 illustrates an exploded view with the electronic device 100 being in-between the case body 1500 and a patch assembly 1200c. That is, FIG. 16 illustrates how the electronic device 100 would fit in a patch housing 1601. The patch assembly 1200c has a different component arrangement than the patch assemblies 1200 and 1200a. The patch assembly 1200c does not include magnets but includes multiple lateral portions 1204, similar to those described above in connection with FIG. 14.

The case body 1500 in FIG. 16 shields the first surface 1210 of the patch assembly 1200c, providing water resistance or water proofing properties to the smart patch. Here, the smart patch includes the electronic device 100 being housed within the patch housing 1601. The electronic device 100, when in the patch housing 1601, is protected from possible liquid damage in the environment. The case body 1500, when covering the patch assembly 1200c, forms a cavity for holding the electronic device 100. The side touch track 220 of the electronic device 100 is covered by the side track window 1502 provided on the case body 1500. The side track window 1502 enables the usage of the side touch track 220 as a user interface for the smart patch, as discussed above in connection with FIG. 15. Moreover, the display of the side touch track 220 or the light emitted by the side touch track 220 may be visible from outside the case body 1500, in order to present symbols or other information pertaining to the state of the electronic device 100.

Figure 17:
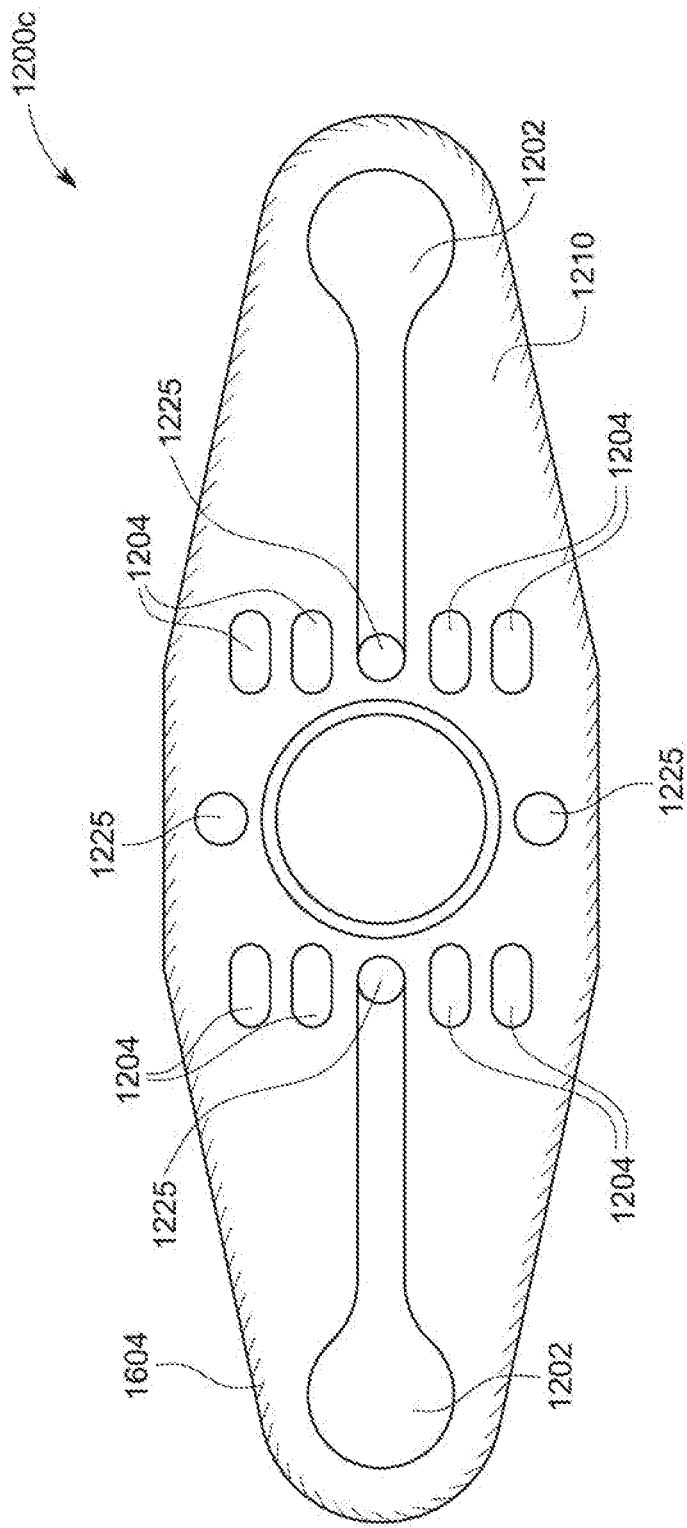
FIG. 17 illustrates a patch assembly of the smart patch of FIG. 16, according to some implementations of the present disclosure.

Referring to FIG. 17, the patch assembly 1200c of FIG. 16 is provided according to some implementations of the present disclosure. To secure the case body 1500 (FIG. 16) to the patch assembly 1200c, the first surface 1210 can have an edge 1604 with adhesive. The adhesive can extend slightly from the edge 1604 as indicated by the shading around the patch assembly 1200c in FIG. 17. Referring to FIG. 16, the adhesive around the edge 1604 can secure a portion of the first surface 1210 of the patch assembly 1200c to a bottom edge 1602 of the case body 1500. The patch assembly 1200c thus includes adhesives on both the first surface 1210 and the second surface (not shown) of the substrate. This adhesive coverage indicated in FIG. 17 is merely provided as an example. In some implementations, adhesive is provided on the first surface 1210 only in areas that will not come in contact with the electronic device 100 (FIG. 16) when the electronic device 100 is assembled in the smart patch. Referring to the second surface of the patch assembly 1200c, adhesive coverage is provided everywhere on the surface except where the lateral portion electrode contacts 1204 and electrode contacts 1202 (which could be, for example, dry electrodes, wet electrodes, semi-dry electrodes, etc.) are present.

Figure 18:
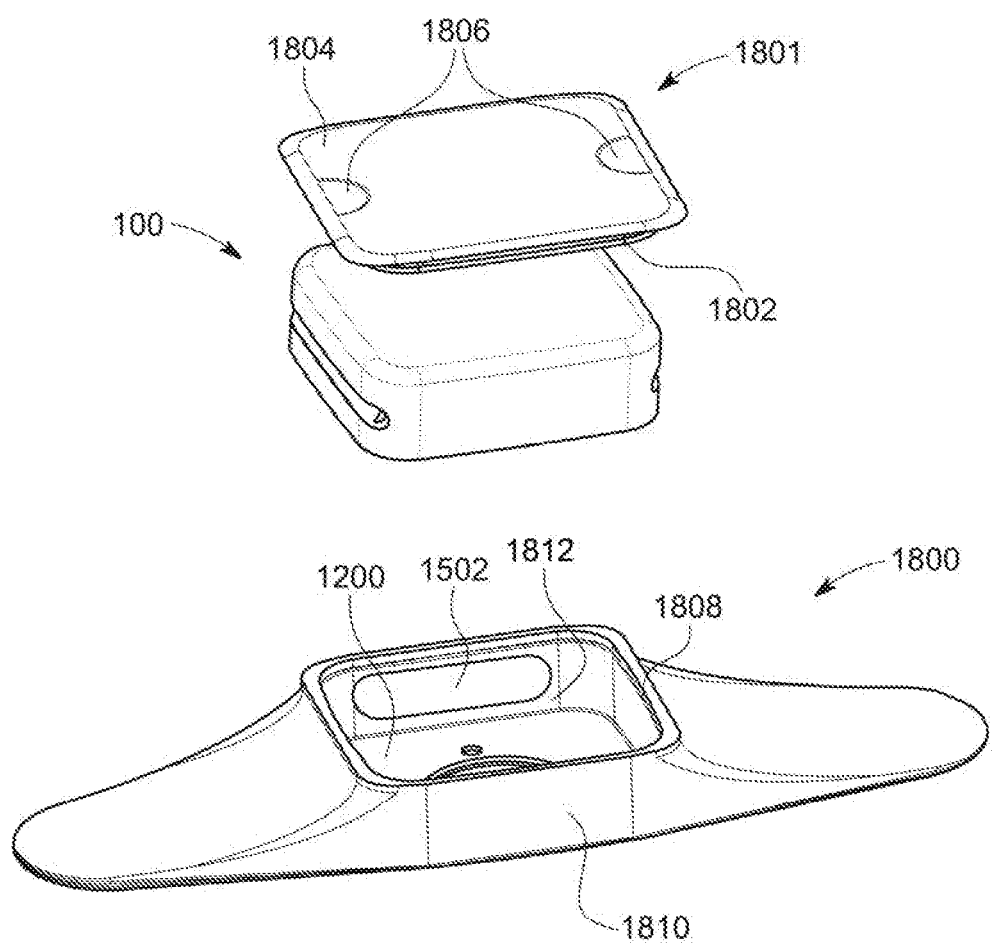
FIG. 18 illustrates an exploded view of a smart patch, according to some implementations of the present disclosure.

Referring to FIG. 18, a case body 1800 with a lid 1801 is provided, according to some implementations of the present disclosure. The case body 1800 includes interior side walls 1812 and an inner groove 1808 for receiving a protrusion 1802 of the lid 1801. FIG. 18 illustrates the inner groove 1808 as a continuous groove around the inner sidewalls and the lid 1801 having the protrusion 1802 being continuous as well. In some implementations, there is a discontinuity in the protrusion 1802 so that multiple protrusions are provided on the lid 1801. The protrusion 1802 and the inner groove 1808 combine to create a snap fit mechanism for the lid 1801. In some implementations, the inner groove 1808 includes multiple grooves and is not a single groove. The lid 1801 can include a flat portion 1804 with recessed regions 1806 so that the lid 1801 can be pulled open. The lid 1801 also allows removing the electronic device 100 from the case body 1800 without having to separate the case body 1800 from the patch assembly 1200.

In some implementations, the patch assembly 1200 in FIG. 18 is integrated with the case body 1800 so that the patch assembly 1200 is not removable from the case body 1800. This can be advantageous in that the electronic device 100 can be removed from the case body 1800 using the lid 1801 and the system includes only three components: the case body 1800, the lid 1801, and the electronic device 100. The patch assembly 1200 is merely used as an example, but in other implementations, other patch assembly designs (e.g., the patch assemblies 1200a,c) can be used in FIG. 18.

Patch assemblies provided in FIGS. 12-18 can be provided with different types of magnets, lateral electrodes, connecting members, etc. The arrangement provided in these figures are merely provided as examples. For example, FIG. 13 utilizes magnets (e.g., the coupling element 302) but FIG. 17 does not. In some implementations, these configurations can be reversed, where magnets are not provided in FIG. 13 but provided in FIG. 17. Furthermore, the connecting members 1225 are used in the patch assemblies of FIGS. 12-18. The connecting members 1225 can be male or female-type connectors to match complementary connectors on the electronic device 100. In some implementations, instead of having male-type or female-type connectors, the connecting members (e.g., the connecting members 1225) are flat contact electrodes that match flat contact electrodes (e.g., the connecting members 225 of FIG. 4) on the electronic device 100. These flat contact electrodes merely require contact and do not need a locking mechanism. In some implementations, flat contact electrodes are useful in smart patches that have a case body (see e.g., FIGS. 17 and 18). The case body can keep the electronic device 100 connected to the patch assembly without having to have a snap connector interface between the electronic device 100 and the patch assembly.

In some implementations, a patch assembly includes two types of electrodes (i.e., first types of electrodes like the electrodes 1202 (FIG. 17) and second types of electrodes like bioimpedance electrodes provided at the lateral portions 1204 (FIG. 17). The first types of electrodes and the second types of electrodes can be used to define axes of symmetry of the patch assembly. For example, referring to FIG. 14, the first types of electrodes are positioned on a first axis of symmetry of the patch assembly 1200a and the second types of electrodes are positioned a distance away from the first axis of symmetry of the patch assembly 1200a. The second types of electrodes are positioned on a second axis of symmetry of the patch assembly 1200a and the first types of electrodes are positioned a distance away from the second axis of symmetry of the patch assembly 1200a.

In some implementations, as shown in FIG. 17, the first types of electrodes are positioned on a first axis of symmetry of the patch assembly 1200c and the second types of electrodes are positioned a distance away from the first axis of symmetry of the patch assembly 1200c. Both the first types of electrodes and the second types of electrodes do not intersect a second axis of symmetry of the patch assembly 1200c.

In some implementations, the electronic device 100 in FIG. 18 can have a bottom with the third design 100c of FIG. 5 where no snap connectors or magnetic couplers are used. The electronic device 100 can merely fit in the case body 1800 which keeps the electronic device 100 in place over electrode contacts provided on the patch assembly 1200. In some implementations, since a smart patch does not require constant and direct interaction with the user, user interfaces of the electronic device 100 (e.g., the side touch track 220 of FIG. 2 and the screen of the top portion 102 of FIG. 2) may be restricted and/or reconfigured during cardiac patch mode. As a consequence of the reconfiguration, the bezel-less screen in the electronic device 100 may be used for displaying large symbols that convey the state of the electronic device 100 (e.g., battery level, sensor connections, wireless connectivity, etc.). The case body 1800 can have rounded and semi-flexible corners and appearance to enhance wearing comfort. The flexible design can avoid scratching the user or getting caught in the user's clothes when the smart patch is worn. The case body 1800 may be made of silicone, a relatively flexible matrix, a resin, or other materials. All these possible compositions may allow the patch assembly 1200 at the bottom to be used for long-term adhesion to the user without much discomfort.

Figure 19:
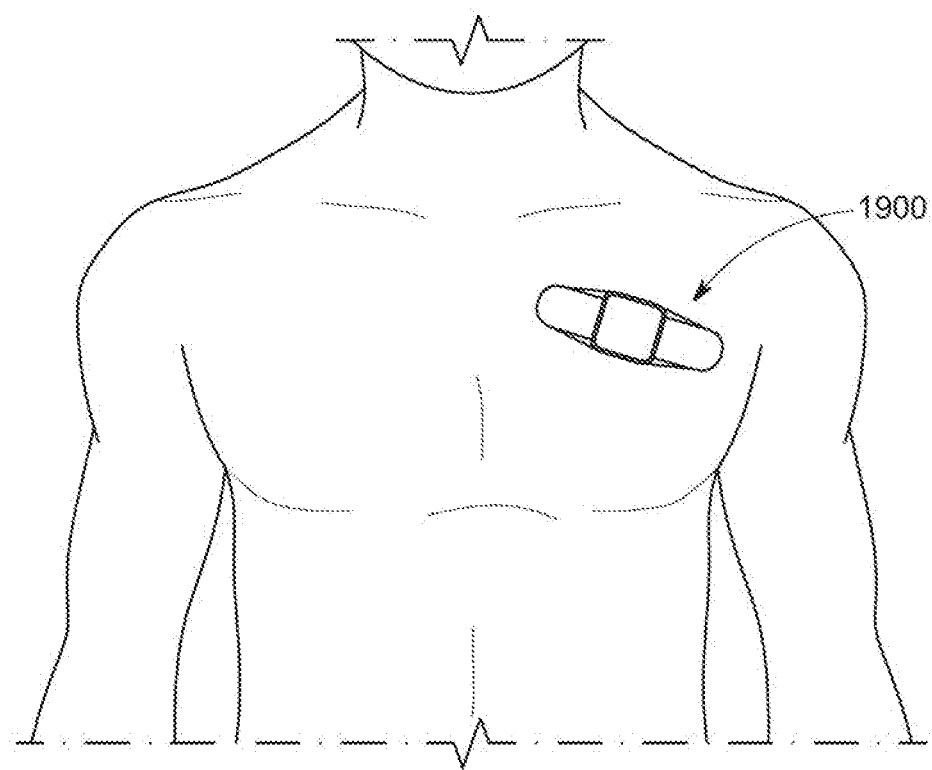
FIG. 19 illustrates an example of the placement of a smart patch, according to some implementations of the present disclosure.

FIG. 19 illustrates an example of the placement of a smart patch 1900 on the left chest area of a user. Placement of the smart patch 1900 on the left chest area can enable the smart patch 1900 to obtain more ECG data when compared to the electronic device 100 being in the smartwatch configuration 900 (FIG. 9C). The smart patch 1900 can be assembled by attaching snap electrodes of an electronic device (e.g., the electronic device 100) to a patch assembly (e.g., the patch assembly 1200). Once attached, a removable layer that covers an adhesive side of the substrate in the patch assembly 1200 is peeled off and adhered to the chest area of the user. The area should be properly cleaned before adhesion.

In some implementations, the smart patch 1900 is similar to the smart patch of FIG. 16 including the case body 1500. As such, the patch assembly 1200c includes adhesive on both surfaces of the substrate such that the case body 1500 can be joined to the patch assembly 1200c as discussed in connection with FIGS. 16 and 17. In some implementations, the smart patch 1900 is similar to the smart patch of FIG. 18 including the case body 1800 with the lid 1801. The lid 1801 can be snap fit to the case body 1800 after contact electrodes of the electronic device 100 are tested and a message or symbol, indicating correct sensor alignment, is displayed on the top portion of the electronic device 100 and/or the side touch track of the electronic device 100.

In some implementations, to detach the smart patch 1900 from the skin of the user, a tab to pull the adhesive from the skin of the user can be integrated in the smart patch 1900. For example, adhesive provided on the patch assembly of the smart patch 1900 can have the tab to facilitate detaching the patch assembly from the skin of the user. Once the smart patch 1900 is removed from the body of the user, the adhesive electrodes (e.g., the patch assembly 1200 of FIG. 12) are disconnected from the electronic device 100 and disposed of. Disconnecting the adhesive can include separating snap electrodes, magnets, snap buttons, etc.

Although the smart patch and smartwatch configurations are illustrated, other configurations can be contemplated within the scope of the present disclosure. For example, the electronic device 100 can be positioned in a belt, strap, band, a bracelet, and/or other wearables. Form factor is important in some of these configurations, as such, the electronic device 100 that has a smaller form factor may be more limited in capabilities than one with a larger form factor. For example, the electronic device 100 when designed to be positioned in an area of a belt buckle can be made much larger than when designed to be incorporated and worn as a bracelet. The larger belt buckle design can fit more sensors and possibly perform more functions when compared to the smaller bracelet design.

Figure 20:
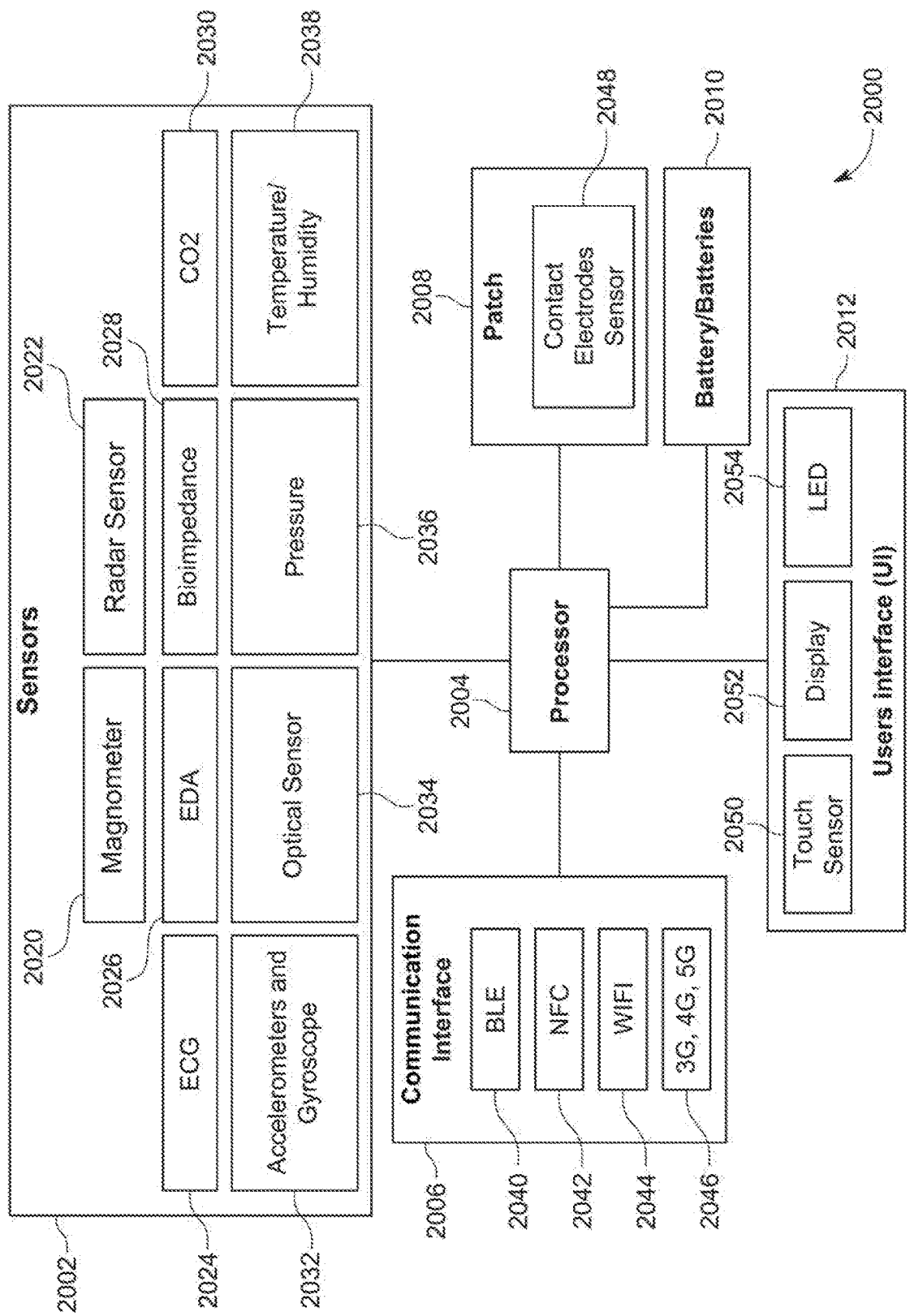
FIG. 20 illustrates a block diagram of components within an electronic device, according to some implementations of the present disclosure.

FIG. 20 illustrates a block diagram of components within an electronic device 2000, according to some implementations of the present disclosure. The electronic device 2000 is similar to or the same as the electronic device 100 of FIG. 1. The electronic device 2000 includes one or more sensors 2002, one or more communication interfaces 2006, one or more processors 2004, one or more batteries 2010 (e.g., the battery 210 of FIG. 2), and one or more user interfaces 2012. In some implementations, the electronic device 2000 is placed in a smart patch configuration as discussed in connection with FIG. 12; as such, the electronic device 2000 along with a patch assembly 2008 is a smart patch. The patch assembly 2008 can include contact electrode sensors 2048 which are similar to or the same as the electrodes 1202 (FIG. 12) and/or any electrodes positioned in the lateral portions 1204 (FIG. 14).

The sensors 2002 can generate data relating to the health and environment of a user. The sensors 2002 can include a magnetometer 2020 for measuring magnetic fields. The magnetometer 2020 can enable several applications including sensing the presence of magnetic wireless charging devices. The magnetometer 2020 can be used in combination with an accelerometer and gyroscope to form part of an inertial measuring unit (IMU). The magnetometer 2020 in the IMU allows fixing the relative movements of the body of a user to the coordinate system of the earth, which can be helpful in detecting the absolute orientation of the user. For example, movements can be monitored and identified, such as when an elderly person has fallen. The magnetometer 2020 can be used alone or in collaboration with other sensors 2002 to detect sleep parameters by measuring a variation in the earth's magnetic field. An example sleep parameter that can be measured includes breathing movements.

The sensors 2002 can include a radar sensor 2022 which can use radio frequency (RF) receivers and transmitters in determining object location and/or object movements. The sensors 2002 include ECG sensors 2024 (e.g., the connecting member 224 of FIG. 2 being used as ECG electrodes). The sensors 2002 can include EDA sensors 2026 for measuring electrical properties of skin. The EDA sensors 2026 can measure galvanic skin response or skin potential, resistance, and/or conductance by passing a small amount of current through the skin of the user. The EDA sensors 2026 can be used to monitor stress level patterns or level of neural and physical activity as well as skin moisture among other possible indicators.

The sensors 2002 can include bioimpedance sensors 2028 (e.g., the lateral electrodes 304 of FIG. 3 can be used to measure bioimpedance). The bioimpedance sensors 2028 support different bioimpedance techniques (e.g., single-, multi-frequency, and bioimpedance spectroscopy) for capturing various types of health metrics. The sensors 2002 can include a carbon dioxide ($CO_2$) sensor 2030 or some other gas sensor (e.g., a carbon monoxide sensor, etc.) to alert the user of potentially dangerous environments. High levels of $CO_2$ in a confined space can be dangerous. Elevated $CO_2$ levels can increase headaches and lethargy while lowering ability to concentrate on high-level tasks. Therefore, the $CO_2$ sensor 2030 may be used alone or in combination with other environmental sensors to monitor air quality and ventilation around the user. The $CO_2$ sensor 2030 can enable displaying $CO_2$ levels on a smartwatch/smartphone and further enable a threshold for an alarm, where 0.7% is set as the maximum level of $CO_2$ concentration for the user to withstand without experiencing adverse health conditions.

The sensors 2002 can include motion and position sensors like accelerometers and gyroscopes 2032. The motion and positions sensors can capture complex translation and rotation values that may determine movement of a human body part and pose angle in order to compensate the signal change based on the change of body pose (e.g. lying, standing and other poses). Accelerometers and gyroscopes may be utilized to keep track of body motion, thus generating data for step counting, walking speed, running speed, and sleep monitoring. The motion sensors enable body posture correcting programs and/or physical rehabilitation exercises by placing the electronic device 100 of FIG. 1 on one or different body locations. Likewise, the motion sensors may be used to activate a display user interface by analyzing arm movements/gestures and can further be used to launch specific applications, trigger certain features, adjust audio output volume, control music (e.g., skip to the next song, pause, play, etc.), and other user requests. Some arm movements/gestures that could be captured and utilized in the electronic device 2000 could be a clockwise or counter-clockwise arm rotation to elevate or reduce the volume of the device when the electronic device 2000 is arranged in the smartwatch configuration.

The sensors 2002 can include optical sensors 2034 for performing non-contact measurements (e.g., through the housing window 222 as discussed in connection with FIG. 2). The optical sensors 2034 can include non-visible light sensors such as infrared and/or visible light sensors provided with blue, red or green LED or other forms of apparent diffusion coefficient (ADC) values. One or more emitters and the one or more photodetectors can be provided on a PCB and used as an optical array measurement system. The photodetectors and/or the emitters can be arranged in a circle around a center which can introduce redundancy that minimizes effects of noise attributed to the skin of the user moving, a heart of the user beating, and so on.

Signals extracted from the optical sensors 2034 may be used to determine blood oxygen levels, blood pressure, and calibration for glucose level. Blood oxygen saturation (SpO2) is an important vital sign for assessing a user's physical health as low blood oxygen levels can indicate hypoxemia, which can compromise organ functions, if it is not properly treated. Blood volume changes in the microvascular bed of tissue of the user's body part in contact with the electronic device 2000 can be calculated through photoplethysmogram (PPG) sensing. By emitting light and measuring the light absorption using the optical sensor 2034, the PPG values can be determined. For measuring glucose levels, infrared LEDs can emit light in a wavelength range between 850 nm and 1000 nm, for example, at about 940 nm. After the light is absorbed by the skin in contact, glucose transforms the light into heat dissipated, enabling a temperature change measure to calculate the blood glucose level of the user. However, IR sensors are not the only source of data to calculate glucose levels. ECG sensor 2024 and/or bioimpedance sensor 2028 data may be used to measure blood glucose levels.

The sensors 2002 can include a pressure sensor 2036. The sensors 2002 can include a temperature and/or humidity sensor 2038. The temperature and humidity sensor 2038 can generate temperature and/or humidity data for calibrating other measurements such as blood pressure, glucose, etc. and or skin humidity/moisture. To additionally measure the atmospheric pressure relative to the environment, the pressure sensor 2036 may be incorporated. The pressure sensor 2036 can be used to determine altitude as well as temperature and airflow changes during constant motion. The sensors 2002 can include other environmental sensors or sensors that generate health metrics or physiological data associated with the user. The sensors can also include laser sensors, imaging sensors, thermal imaging sensors, radar sensors (e.g., Doppler radar), micromechanical systems (MEMS), or other non-contact sensors for performing measurements on the skin of the user. In some implementations, temperature change and pulse sensing can be used to predict fever, vasodilation, or both.

In some implementations, the sensors along with other components can cooperate to obtain user inputs (e.g., user preferences, health data, etc.) or environmental inputs, and/or to provide feedback (e.g., health metrics, recommendations, etc.) to a user. The sensors can be located on one PCB (e.g., the second PCB 208 of FIG. 2) or across multiple PCBs (e.g., the first PCB 206 and the second PCB 208 of FIG. 2) of the electronic device 2000. When the sensors 2002 are provided on only one PCB, the PCB where the sensors 2002 are provided is dubbed the sensor PCB. The sensor PCB may include biological sensors for capturing health metrics of a user, a proximity detector for detecting the proximity of objects, and environmental sensors (e.g., temperature, humidity, ambient light, pressure, altitude, compass, etc.). The electronic device may integrate a dedicated processor for processing one or more data streams from all the sensors, and to run real-time algorithms and machine learned models for computing health metrics and other insights based on the sensor data.

The communication interfaces 2006 can support wired and/or wireless communication protocols including Bluetooth®, Bluetooth® Low Energy (BLE), NFC, WiFi, and/or cellular protocols including 3G, 4G, Long-Term Evolution (LTE), 5G, etc. The user interface 2012 can include a touch sensor 2050, a display 2052, and/or a light emitting diode (LED) 2054. In some implementations, the user interface 2012 includes one or more microphones for receiving voice commands from the user. In some implementations, the user interface 2012 includes one or more speakers for playing sounds for the user.

The processor 2004 can include one or more multiple microcontroller units (MCU). The processor 2004 interprets input signals (e.g., input signals from the sensors 2002 or input signals from the user interface 2012) and generates monitoring data outputs. The monitoring data outputs can be communicated to external devices (e.g., a mobile phone or laptop computer) via the communication interface 2006 or communicated to the user via the user interfaces 2012. The processor 2004 can support on-device machine learning models, thus enabling the processor 2004 to simultaneously process multiple data streams from the sensors 2002 and derive health insights and biomarkers of diseases that are more reliable than a single sensor's data stream processed in isolation. By running on-device machine learning algorithms, the electronic device 2000 may infer different health conditions in real-time (e.g., heart arrhythmia, heart attack, glucose changes, stroke, etc.).

The processor 2004 can communicate raw data and/or processed data from the sensors 2002 to one or more predefined recipients for further processing or display. In some embodiments, processed or raw acquired data from the sensors 2002 may be transmitted to a mobile device (as a smartphone, computer and so on) where data can be displayed or managed, and later on, the information might be sent to the cloud for storage and/or analysis. In an alternative embodiment, the processor 2004 may send the acquired data directly to the cloud through the communication interface 2006, and further, to a mobile device of a clinician. Data received from the sensors 2002 can be used to control one or more features provided by the electronic device 2000 (e.g., control information displayed, control sleep-timer behavior, control alarm or alert behavior, etc.). In some implementations, one or more of the input signals from the sensors 2002 may be filtered, analyzed and processed to extract desired health-related and environmental data. The processor 2004 may control command interactions among device components and communications over an input/output (I/O) interface with a determined operational system.

In some implementations, the electronic device 2000 includes one or more dedicated artificial intelligence (AI)-accelerator chips (e.g., graphics processing unit (GPU), neural chip, etc.) for executing artificial intelligence models running on the electronic device 2000. These may include artificial neural networks models, machine vision models, machine learning models and multimodal models. The chips may be used for multi-sensor data processing, novel dataflow architectures, tasks requiring in-memory computing capability, accelerating algorithms and other tasks. The AI accelerator has high-throughput on-chip memory for data intensive AI tasks. Also, memory storage can be a feature of one or more PCBs of the electronic device 2000. Some memory storage may be used to save, temporarily and/or permanently, data generated by the sensors 2002 when there is no connectivity to an external storage or external device. Some memory storage may be used to process certain amounts of data in the same PCB. In some implementations, the memory may include one or more memory forms including non-volatile memory, static random-access memory (RAM), cache, volatile RAM, virtual memory microdrive, and electrically erasable programmable read-only memory (EEPROM). Data compression may be used to reduce memory usage of the data captured by the sensor 2002 when processed and before being transferred to a coupled device.

In some implementations, the ECG sensor 2024 captures electrical activity of the heart. One or multiple electrical values can be used for measuring the pattern of the cardiac rhythm of a user. Recordings by the ECG sensor 2024 are captured by electrodes in contact with the skin of the user. For example, the electrodes 1202 of FIG. 12 are in direct contact with the skin of the user. In some implementations, various form factors of the patch assembly 2008 with pre-positioned electrodes may include any value between one and twelve leads, inclusively. As an example, a twelve lead patch assembly layout can mimic traditional lead placements for a Holter monitor.

A smart patch configuration (e.g., as shown in FIG. 19) of the electronic device 100 places electrodes on the chest of a user. However, in varying the arrangement of electrodes to extract accurate ECG signals, the electronic device 100 can be configured for abdominal or lateral placements. Placement of the electronic device 100 on the skin of the user in either a smartwatch configuration (e.g., the smartwatch configuration 900 of FIG. 9C) or a smart patch configuration (e.g., in FIG. 19) enables detection of any potentially fatal cardiac abnormality, such as arrhythmias. Placement of the electronic device 100 on the skin of the user may serve other diagnostic purposes. For example, including an additional electrode on the side touch track 220 (FIG. 12) of the electronic device 100, bipolar leads for accurate ECG measurements can be supported in the smartwatch configuration.

Electrodes (e.g., the connecting members 224 and/or the lateral electrodes 304 of FIG. 3) disposed on the bottom of the electronic device 2000 can enable bioimpedance and/or ECG measurements. Arrangement of the electrodes can allow monitoring of heart rate and pulse of the user. Additional use of the ECG sensor 2024 may include extracting heart rate variability (HRV) of a user. HRV is the time variation between heartbeats. Studies have shown a strong inverse correlation between HRV and physiological intensity as it relates to stress and recovery. In general, a higher HRV results in increased stress recovery levels, whereas a lower HRV results from increased stress.

A microphone array may be used to capture and store heart sounds (such as murmurs, etc.) which could be temporally related to ECG tracings (captured from the ECG sensor 2024) and other health metrics captured by other sensors in the device in order to allow for the analysis of hemodynamic parameters indicative of heart disease. The audio recordings could be saved in the electronic device 2000 or streamed wirelessly to a smartphone or to a cloud computing device to enable clinician visualization of the heart sound waveform (phonocardiogram), playing of the recordings, cross referencing with other health metrics, and AI-analysis for heart murmur screening, and auscultation live-streaming for telemedicine consults. A microphone array may also be used to capture and store lung sounds.

Bioimpedance may be defined as a passive electrical property of the cell/tissue when energized with an electric potential. Bioimpedance sensors 2028 offer complex impedance values as high and/or low-frequency changes in an electromagnetic field generate a dielectric response in biological tissue. In fact, the complex dielectric impedance could be analyzed since the real part corresponds to the capacity of the tissue to absorb energy and the complex part corresponds to the dissipated energy. In the four-electrode layout (e.g, the four-electrode configuration of the lateral electrodes 304 shown in FIG. 6), signal injection and response measurement are performed with two different pairs of electrodes. One pair of electrodes is used to inject the current into the tissue, while a second pair of electrodes is used to measure the voltage. An example of the transmitting frequency range could be found between 5 GHz to 12 GHz whereas the receiving frequency could range from 10 kHz to 100 kHz. Other frequency ranges could be employed while remaining within the spirit and scope of the present disclosure. The lateral electrodes included in the bioimpedance sensor 2028 transmit low power non-ionizing and safe radio waves through a section of the human body, such as the wrist or the chest, via one or more surface electrodes. These areas have an adequate blood supply and allow blood supply to pass through the tissue. The signals are then received by other lateral electrodes in bioimpedance sensor 2028. In combination with other sensors 2002, characteristics of the user's blood can be non-invasively assessed and analyzed. Therefore, the bioimpedance signals alone or combination can be used to measure the glucose level, directly driven by the impedance change of the skin. Most diabetic patients determine their blood glucose level by an outdated finger prick to extract and analyze a drop of blood. Impedance signals together with infrared light sensors may enable continuous measurements from different user body locations, e.g., the wrist or chest. Moreover, the glucose levels may be used to determine metabolism rate of a user throughout the day. By extracting the metabolism rate, many health and lifestyle functionalities can be provided to the user (e.g. the electronic device 2000 may inform the user what time is better to exercise or when to stop physical activity, as well as provide nutritional guidance).

The bioimpedance sensor 2028 can be used to extract hydration level of the user, muscle composition of the user, fat composition of the user, body mass index (BMI) of the user, and/or average daily calorie requirement of the user. The bioimpedance sensor 2028 can be used to keep track of the user's weight and metabolism rate at different moments of the day. These health metrics may be displayed on the display 2052 or may be utilized to generate other functions, such as personalized workouts and suggested times for exercising and eating. Data logging and alarm functions may be included in the electronic device 2000 to track glucose levels when glucose levels get too high or too low, outside of a prescribed, safe range.

The radar sensor 2022 detects location and movement of nearby objects, providing assistance to the user or triggering safety equipment (e.g., eliciting sounds from a wireless speaker). In some implementations, the position of the electronic device 2000 in reference to the user may be facilitated by the radar sensor 2022 to ensure the proper location and contact of the electronic device 2000 to the skin of a user. Monitoring the placement of the electronic device 2000 is relevant to determine the quality of measurements made by the different sensors 2002. Therefore, the radar sensor 2022 can include proximity sensors located in a base of the electronic device 2000 (e.g., located in the bottom portion of the electronic device 100). The proximity sensors can determine relative position of the electronic device 2000 and the user's skin, providing feedback on whether placement of the electronic device 2000 should be modified. Alternative locations of the radar sensor 2022, different functionalities and or implementations can vary in different embodiments. Apart from having the radar sensor 2022 work as a proximity sensor, the radar sensor 2022 can be used to monitor heartbeat and breathing in other implementations. For example, the radar sensor 2022 can monitor movement of the chest cavity of the user to determine when the user is breathing in and when the user is breathing out. The radar sensor 2022 can monitor motion of the heart during heartbeats to, for example, determine a pulse for the user.

The sensors 2002 or other components of the electronic device 2000 can be used to switch the mode of a display of the electronic device 2000 between a smartwatch mode and a smart patch mode. In the smartwatch mode, a watch user interface can be displayed, and in the smart patch mode, a patch user interface can be displayed. Switching between the two modes (and consequently the two different user interfaces) can be controlled by determining whether the electronic device 2000 is engaged to the patch assembly 2008. For example, in some embodiments, the electronic device 2000 may use connective magnets (e.g., the coupling element 302 of FIG. 3 and/or the coupling element 302 of FIG. 12) to attach to the patch assembly 2008 (see e.g., the electronic device 100 and the patch assembly 1200 of FIG. 12), and the magnetometers 2020 can sense a change in the magnetic field, thereby switching the display 2052 between the smartwatch mode and the smart patch mode. In some implementations, electrode contacts in the electronic device 2000 (e.g., the connecting members 224 of FIG. 3) can be magnetized to detect when electrodes on the patch assembly 2008 (e.g., the electrodes 1202 of FIG. 12) enter the magnetic field of the electronic device 2000. Detecting the electrodes on the patch assembly 2008 can trigger changing the display mode between the smartwatch mode and the smart patch mode.

In some implementations, a push button situated on the bottom of the electronic device 2000 and proximate to electrode connectors on the bottom of the electronic device 2000 (e.g., the connecting members 224 of FIG. 3) can be used to switch the display mode from the smartwatch mode to the smart patch mode. When the electronic device 2000 is mechanically coupled to the patch assembly 2008, the push button is activated. Activating the push button triggers changing the display mode from the smartwatch mode to the smart patch mode. Otherwise, the display mode remains in the smartwatch mode as long as the push button is not activated. In some implementations, a manual configuration of the display through the touch screen of the electronic device can be used to switch between the smart patch mode and the smartwatch mode.

Overall, the sensors 2002 generate data that can be analyzed for a separate application or combined for multiple applications. For example, a combination of ECG and temperature data can be used to measure the sleep cycle by analyzing the heart and breathing patterns. In other applications, the combination of ECG, blood pressure and heart rate monitoring may provide a means of improving compliance with cardiac rehabilitation while maximizing safety and better individualizing management strategies and education arising in real-world activities.

The display 2052 may be integrated with its computing unit or externally connected to the processor 2004. Besides signaling and receiving touch sensed data, the display 2052 may use visual indicators for signaling. For example, visual indicators can signal that the electronic device 2000 is capturing data, battery level, if there is an issue to troubleshoot, etc. A touch sensor 2050 can be integrated with both the display 2052 and the side touch track 220 of FIG. 2. The side touch track 220 may also contain a LED 2054 or display. The display 2052 can include an organic LED (OLED), liquid crystal display (LCD), thin-film transistor (TFT), or other appropriate display technology. For additional data safety, a light-transmissive portion of the integrated touch sensor 2050/display 2052 can be combined so that its configuration for either emitting or receiving light enables an image-sensing element that could be used to detect the fingerprint of a user. The side touch track 220 (FIG. 3) or the screen integrated in the top portion 102 (FIG. 3) of the electronic device 100 (FIG. 3) can include the integrated touch sensor 2050/display 2052 to enable the described functionality.

The light-transmissive portion may be transparent to infrared radiation and opaque to visible light. The light sources may include the LED 2054 of discrete wavelengths to emit different colors as red, green or yellow to indicate battery levels, connection or sensor states and or more states of the electronic components. The outputs provided by the user interface 2012 may also be responsive to, or initiated by, a program or application executed by the processor 2004 and/or associated device through the communication interface 2006. In addition to the user interface 2012 and the sensors 2002, the electronic device 2000 may integrate gauges, resistive sensors, location sensors (e.g., a global positioning system (GPS)) and mechanical devices such as buttons or switches or some combination thereof. The electronic device 2000 can support haptic feedback for notifying the user of battery levels, connectivity errors, etc. By integrating a GPS component, the location of a user could be detected to create map routes or send the location information to health providers if there is a fall detection alert.

The processor 2004 may be coupled to both the sensors 2002 as well as to the user interface 2012 and other possible output modules (e.g., speakers, haptic devices or lights). The processor 2004 may interpret input signals to determine the possible output response (e.g. display an indication of an error in the connection between the electronic device 2000 and the electrodes 2048). The processor 2004 for a compact electronic device can include two PCBs as disclosed in FIG. 2. One of the two PCBs can include the sensors 2002, and the other of the two PCBs can process signals and manage the NFC 2042, BLE 2040, WiFi 2044 and mobile network communications 2046 (e.g., 3G, 4G, 5G, LTE, etc.).

The communication interface 2006 may include components for a one-sided or reciprocal wireless data transfer. In some embodiments, the communication interface 2006 may be utilized just to send data whereas in other embodiments, besides transmitting data, the communication interface 2006 may also receive data remotely. Other types of wireless communication that can be included in the communication interface 2006 include wireless local area network (WLAN), wide area network (WAN), wireless personal area network (WPAN), Worldwide Interoperability for Microwave Access (WiMAX), active and/or passive radio frequency identification (RFID), ultra-wideband (UWB), and other network adapters. Besides wireless communication, there might be a serial type of communication in alternative designs such as universal serial bus (USB), flash drive or others.

The processor 2004 can execute a calibration with data acquisition for at least one of the sensors 2002. As poor sensor calibration may compromise the quality of the health and environmental data extracted and interfere with other signals, calibration may be executed at the commencement of the recordings or at periodic intervals during operation.

The electronic device 2000 can integrate a voice assistant to receive instructions through multiple inputs from the user (e.g., microphones, screen, etc.) and provide answers or complete actions. The electronic device 2000 may also include a mobile network interface for taking and making calls. Besides health metrics described herein, the electronic device 2000 in a smartwatch configuration can provide complimentary standard smartwatch functionalities as calendar or time display and so on.

Figure 21A:
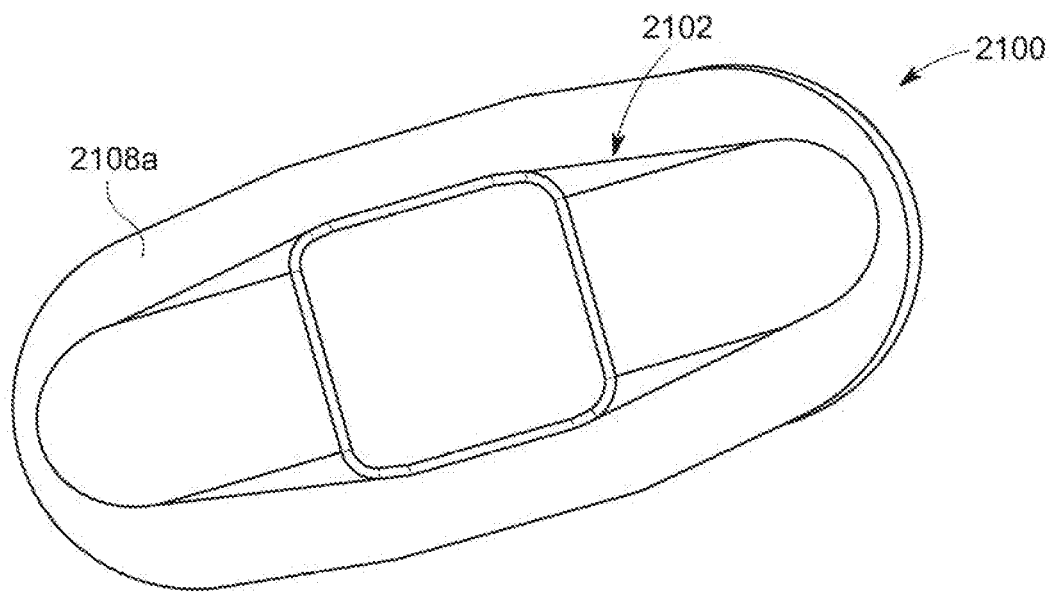
FIG. 21A illustrates a top view of a smart patch, according to some implementations of the present disclosure.

Referring to FIG. 21A, a top view of a smart patch 2100 is provided, according to some implementations of the present disclosure. The smart patch 2100 is similar to or the same as the smart patch 1900, as discussed above in connection with FIG. 19. The smart patch 2100 includes a cover 2102 which is similar to or the same as the case body 1500 of FIG. 15. The smart patch 2100 can further include a removable layer 2108a that surrounds the cover 2102. The removable layer 2108a can be adhered to a top surface of transparent film 2110 (FIG. 21B) extending from the cover 2102.

Figure 21B:
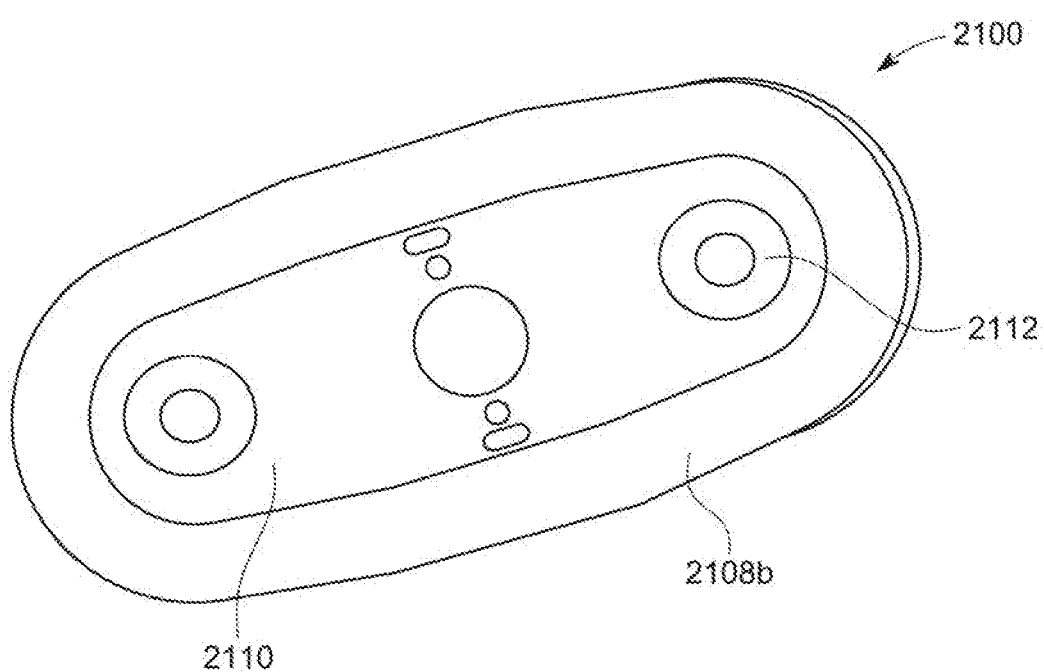
FIG. 21B illustrates a bottom view of the smart patch in FIG. 21A, according to some implementations of the present disclosure.

Referring to FIG. 21B, a bottom view of the smart patch 2100 of FIG. 21A is provided. The smart patch 2100 can include another removable layer 2108b that is adhered to a second side of the transparent film 2110 extending from the cover 2102. The transparent film 2110 protects electronic components of the smart patch 2100 from the outside environment. The transparent film 2110 is an example of the substrate discussed in connection with FIG. 12. Through the transparent film 2110, a bottom view 2112 of electrodes can be seen.

Figure 21C:
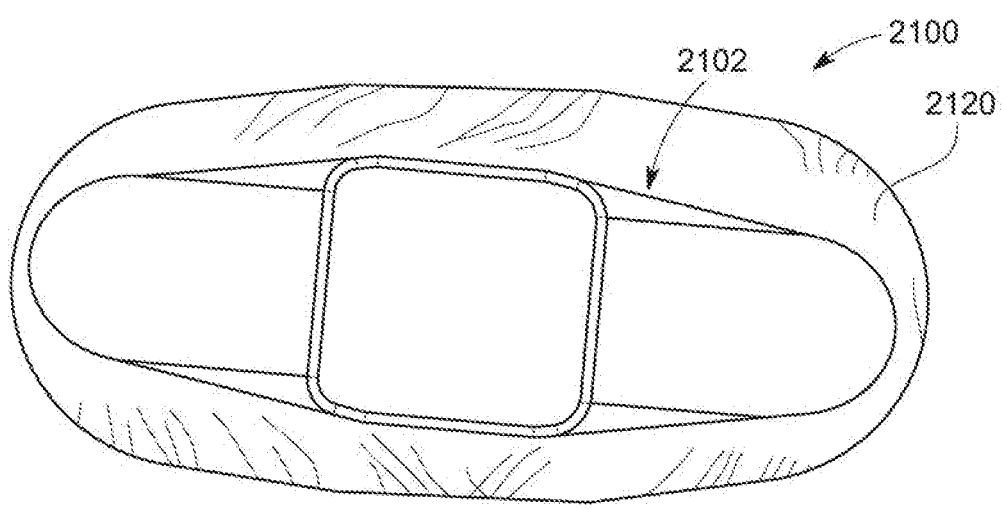
FIG. 21C illustrates the smart patch of FIG. 21A affixed on a user, according to some implementations of the present disclosure.

When affixing the smart patch 2100 to the skin of the user, the removable layer 2108b is peeled off to expose a sticky portion of the transparent film 2110. The sticky transparent film 2110 is affixed to the skin of the user. The removable layer 2108a can then be peeled off to expose a non-sticky portion of the transparent film 2110, extending from the cover 2102. The non-sticky portion of the transparent film 2120 can be massaged out to remove any air bubbles. FIG. 21C illustrates the smart patch 2100 affixed to the skin of the user with a non-sticky portion 2120 of the transparent film 2110 being visible.

Figure 22A:
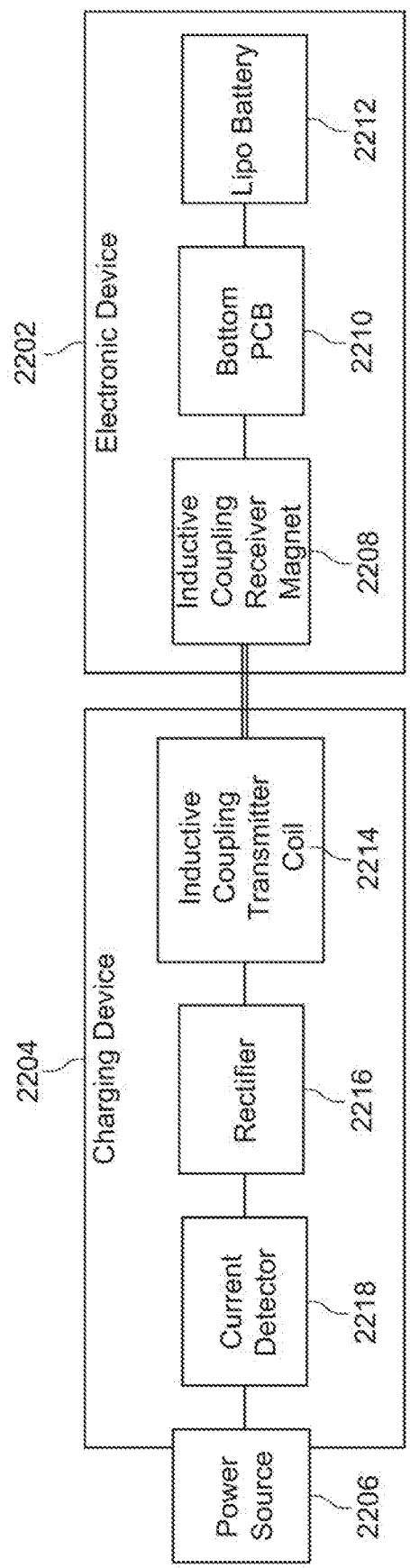
FIG. 22A illustrates a block diagram of a magnetic charge interface for the electronic device of FIG. 1, according to some implementations of the present disclosure.

FIG. 22A illustrates a block diagram of a magnetic charge interface (charging device 2204) for an electronic device 2202, according to some implementations of the present disclosure. The electronic device 2202 is similar to or the same as the electronic device 100 of FIG. 1. The electronic device 2202 includes an inductive coupling receiver magnet 2208, provided on a bottom PCB 2210 (e.g., the second PCB 208 of FIG. 2) and connected to a lithium polymer (LiPo) battery 2212 (e.g., the battery 210 of FIG. 2). The charging device 2204 includes a current detector 2218, a rectifier circuit 2216, and an inductive coupling transmitter coil 2214. The charging device 2204 obtains power from a power source 2206, and once the current detector 2218 detects the current, the current is rectified by the rectifier 2216 and sent to the inductive coupling transmitter coil 2214. The inductive coupling transmitter coil 2214 forms part of a transmitter circuit for transforming the received power into a selected frequency band or band frequencies of alternating current and feeding the current such that an alternating current is formed through the inductive coupling transmitter coil 2214 to induce a magnetic field. The induced magnetic field makes the inductive coupling transmitter coil 2214 work like an electromagnet. As the magnetic field generated by the inductive coupling transmitter coil 2214 changes, the inductive coupling receiver magnet 2208 senses the changing magnetic field and current is induced in the inductive coupling receiver magnet 2208. Consequently, alternating current in the receiver field might be created and transformed through filters and rectifiers before reaching the bottom PCB 2210 and LiPo Battery 2212.

Figure 22B:
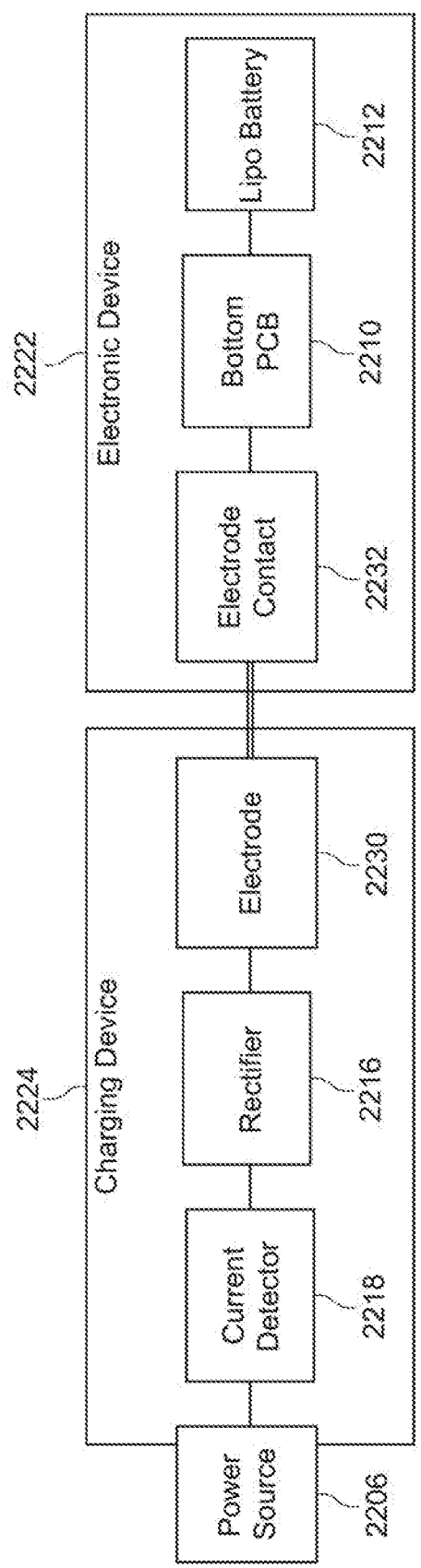
FIG. 22B illustrates a block diagram of an electrode charge interface for the electronic device of FIG. 1, according to some implementations of the present disclosure.

FIG. 22B illustrates a block diagram of an electrode charge interface (charging device 2224) for an electronic device 2222, according to some implementations of the present disclosure. The electronic device 2222 can be similar to or the same as the electronic device 2202 of FIG. 22A and the electronic device 100 of FIG. 1. The electronic device 2202 includes the LiPo battery 2212, the bottom PCB 2210, and an electrode contact 2232 (e.g., the connecting members 224 (FIG. 3), 225 (FIG. 4), 227 (FIG. 5), etc.). The charging device 2224 can be similar to or the same as the charging device 2204. The charging device 2224 draws power from the power source 2206 and includes the current detector 2218 for detecting current and the rectifier 2216 for rectification. The charging device 2224 includes electrode 2230 for mechanical interface with the electrode contact 2232 of the electronic device 2222. Instead of wireless power transmission as in FIG. 22A, FIG. 22B involves contact transmission of power from the electrode 2230 to the electrode contact 2232.

Figure 23A:
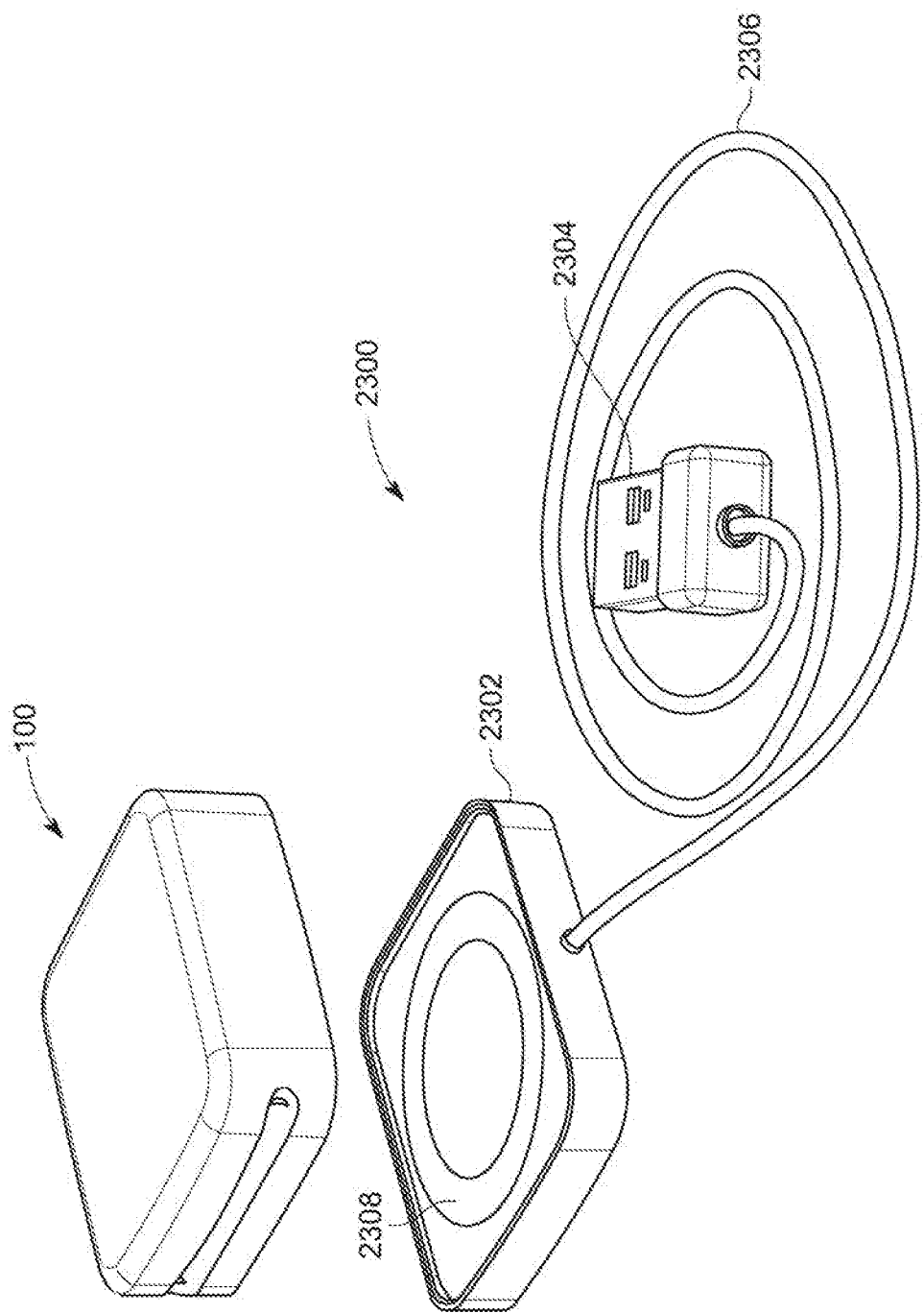
FIG. 23A illustrates the arrangement of an electronic device charger with magnetic interface, according to some implementations of the present disclosure.

FIG. 23A illustrates an electronic device charger 2300 with a magnetic interface provided on a pad 2308, according to some implementations of the present disclosure. Power can be provided to the electronic device charger 2300 through a USB connector 2304 and transported to a body 2302 of the electronic device charger 2300 using the wire 2306. The pad 2308 can indicate a location for the magnetic interface as discussed above in connection with FIG. 22A. The electronic device 100 can be received at the body 2302 for charging purposes.

Figure 23B:
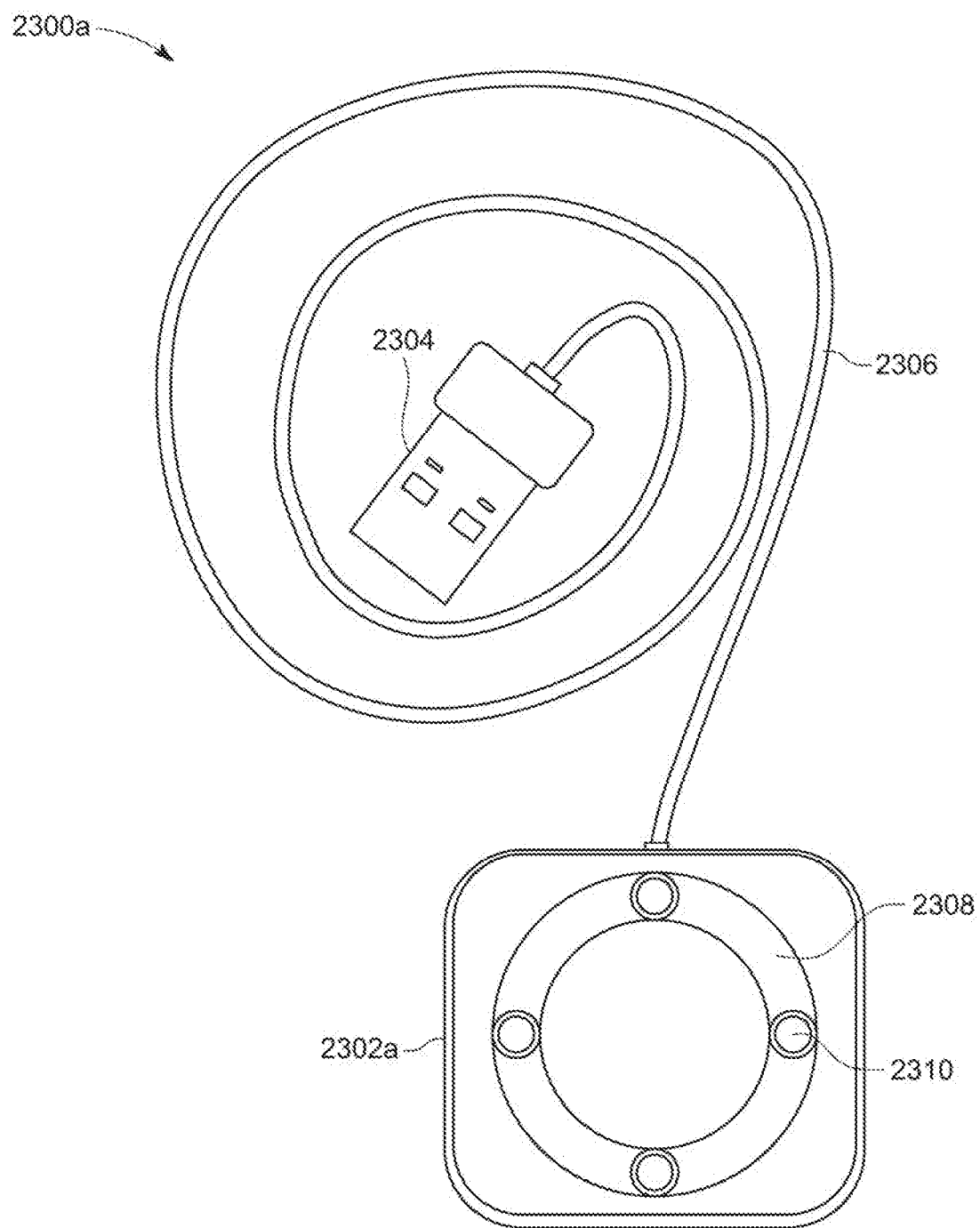
FIG. 23B illustrates atop view of an electronic device charger with snap buttons, according to some implementations of the present disclosure.

FIG. 23B illustrates a top view of an electronic device charger 2300a with contact locations 2310 provided on the pad 2308, according to some implementations of the present disclosure. In some implementations, the contact locations 2310 are snap buttons (e.g., male-type and/or female-type connectors). The pad 2308 can be devoid of any magnetic components such that the electronic device 100 of FIG. 23A can be received at a body 2302a of the electronic device charger 2300a. Connecting members (e.g., the connecting member 224 of FIG. 3) of the electronic device 100 can align with the contact locations 2310 and couple with the contact locations 2310. Power can be transmitted to the electronic device 100 using the USB connection 2304 through the wire 2306 as described above in connection with FIG. 22B. In some implementations, NFC or other wireless charging methods can be integrated in the electronic device charger 2302a or 2302 for charging the electronic device 100.

While the present disclosure has been described with reference to one or more particular implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method for installing a strap in an electronic device, comprising:
   engaging a connective end of the strap to a groove provided on a sidewall of the housing of the electronic device;
   laterally sliding the connective end of the strap along the groove to center the connective end within the groove; and
   pivoting the strap at the connective end such that a tab provided on the strap physically traces a curvature of the groove until the tab engages a notch provided within the groove, wherein the notch includes at least two adjoining concave sidewalls with one of the concave sidewalls being continuous with the groove and having a curvature that substantially matches the curvature of the groove, and wherein engaging the tab to the notch locks the strap within the groove, preventing the strap from laterally sliding along the groove.

2. The method of claim 1, wherein the strap is installed in the electronic device to convert the electronic device from a patch configuration to a watch configuration, the patch configuration being fashioned for attaching the electronic device to a patch housing and the watch configuration being fashioned for securing the electronic device to a wrist of a user using the strap.

3. The method of claim 1, wherein the tab is mechanically biased such that the tab can disengage from the notch.

4. The method of claim 1, wherein the tab is a semi-rigid tab that is compressed when physically tracing the curvature of the groove.

5. The method of claim 1, wherein a length associated with the notch is about 60 to 70 percent of a length associated with the groove.

6. The method of claim 1, wherein the strap is a watch strap.

* * * * *